US012263177B2

(12) United States Patent
Martinez-Montemayor et al.

(10) Patent No.: US 12,263,177 B2
(45) Date of Patent: Apr. 1, 2025

(54) BIOLOGICALLY ACTIVE GANODERMA LUCIDUM COMPOUNDS AND SYNTHESIS OF ANTICANCER DERIVATIVES; ERGOSTEROL PEROXIDE PROBES FOR CELLULAR LOCALIZATION

(71) Applicants: UNIVERSIDAD CENTRAL DEL CARIBE, Bayamón, PR (US); ST. JUDE CHILDREN'S RESEARCH HOSPITAL, INC., Memphis, TN (US)

(72) Inventors: Michelle M. Martinez-Montemayor, San Juan, PR (US); Fatima Rivas, Germantown, TN (US)

(73) Assignees: UNIVERSIDAD CENTRAL DEL CARIBE, Bayamón, PR (US); ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 772 days.

(21) Appl. No.: 17/428,812

(22) PCT Filed: Feb. 6, 2020

(86) PCT No.: PCT/US2020/017053
§ 371 (c)(1),
(2) Date: Aug. 5, 2021

(87) PCT Pub. No.: WO2020/163626
PCT Pub. Date: Aug. 13, 2020

(65) Prior Publication Data
US 2022/0125805 A1    Apr. 28, 2022

Related U.S. Application Data

(60) Provisional application No. 62/802,525, filed on Feb. 7, 2019.

(51) Int. Cl.
| | | |
|---|---|---|
| A61K 31/575 | (2006.01) | |
| A61K 36/074 | (2006.01) | |
| A61K 47/20 | (2006.01) | |
| A61P 35/00 | (2006.01) | |
| G01N 33/58 | (2006.01) | |

(52) U.S. Cl.
CPC .......... *A61K 31/575* (2013.01); *A61K 36/074* (2013.01); *A61K 47/20* (2013.01); *A61P 35/00* (2018.01); *G01N 33/582* (2013.01)

(58) Field of Classification Search
None
See application file for complete search history.

(56) References Cited

FOREIGN PATENT DOCUMENTS

| | | |
|---|---|---|
| CN | 104083382 | 10/2014 |
| CN | 108703979 | 10/2018 |
| JP | 2006022017 | 1/2006 |
| KR | 101090196 | 12/2011 |
| KR | 101289854 | 7/2013 |
| WO | 2009/087368 | 7/2009 |
| WO | 2011/133983 | 10/2011 |
| WO | 2020/191845 | 10/2020 |

OTHER PUBLICATIONS

Suarez-Arroyo (PLOS One (Feb. 2013), vol. 8, No. 2, e57431, 12 pages).*
Amen et al., "Lucidumol C, a new cytotoxic lanostanoid triterpene from *Ganoderma lingzhi* against human cancer cells," J. Nat. Med., 70:661-666, (2016).
Chen et al., "Anti-tumor and Anti-angiogenic Ergosterols from Ganoderma lucidum," Frontiers in Chemistry, 5:85, 1-12 (Oct. 38, 2017).
Mishra et al., "Phenolic Rich Fractions from Mycelium and Fruiting Body of Ganoderma lucidum Inhibit Bacterial Pathogens Mediated by Generation of Reactive Oxygen Species and Protein Leakage and Modulate Hypoxic Stress in HEK 293 Cell Line," Advances in Pharmacological Sciences, Article ID 6285615, 10 gages (Dec. 17, 2018).
Search Report & Written Opinion issued in Int'l Appl. No. PCT/US20/17053 (2020).
Bu et al., "Synthesis and biological evaluation of novel steroidal $5\alpha,8\alpha$-endoperoxide derivatives with aliphatic side-chain as potential anticancer agents," Steroids, Elsevier Science Publishers, 124(9): 46-53 (Jun. 2017).
Bu et al., "Synthesis of $5\alpha,8\alpha$-Ergosterol Peroxide 3-Carbamate Derivatives and a Fluorescent Mitochondria-Targeting Conjugate for Enhanced Anticancer Activities," ChemMedChem Communications, 12(6): 466-474 (Mar. 9, 2017).
Bu et al., "Synthesis of Ergosterol Peroxide Conjugates as Mitochondria Targeting Probes for Enhanced Anticancer Activity," Molecules, 24(18): 3307 (Sep. 11, 2019).
Extended European Search Report issued in Appl. No. EP20752180 (Jul. 5, 2022).

(Continued)

*Primary Examiner* — Susan Hoffman
(74) *Attorney, Agent, or Firm* — Barnes & Thornburg LLP

(57) ABSTRACT

The bioactive compounds of *Ganoderma lucidum* extract (GLE) responsible for anticancer activity were elucidated using NMR, X-ray crystallography and analogue derivatization, as well as anti-cancer activity studies. Structures of the seven most abundant GLE compounds are disclosed. Their selective efficacy against triple negative (TNBC) and inflammatory breast cancers (IBC) and other human cancer cell types (solid and blood malignancies) was shown, confirming potential their as anticancer agents.

13 Claims, 22 Drawing Sheets

(56) References Cited

OTHER PUBLICATIONS

Ling et al., "Development of ergosterol peroxide probes for cellular localisation studies, HHS Public Access," Org Biomol Chem May, 5223-5229 (May 29, 2019).

Martinez-Montemayor et al., "Identification of Biologically Active *Ganoderma lucidum* Compounds and Synthesis of Improved Derivatives That Confer Anti-cancer Activities in vitro," Frontiers in Pharmacology, vol. 10 (Feb. 19, 2019).

Wu et al., "Ergosterol Peroxide Isolated from Ganoderma lucidum Abolishes MicroRNA miR-378-Mediated Tumor Cells on Chemoresistance," PLOS One, 7(8): e44579 (Aug. 30, 2012).

Zhao et al., "Network pharmacology analysis of the anti-cancer pharmacological mechanisms of *Ganoderma lucidum* extract with experimental support using Hepa1-6-bearing C57 BL/6 mice," Journal of Ethnopharmacology, 210(4): 287-295 (Sep. 2017).

\* cited by examiner

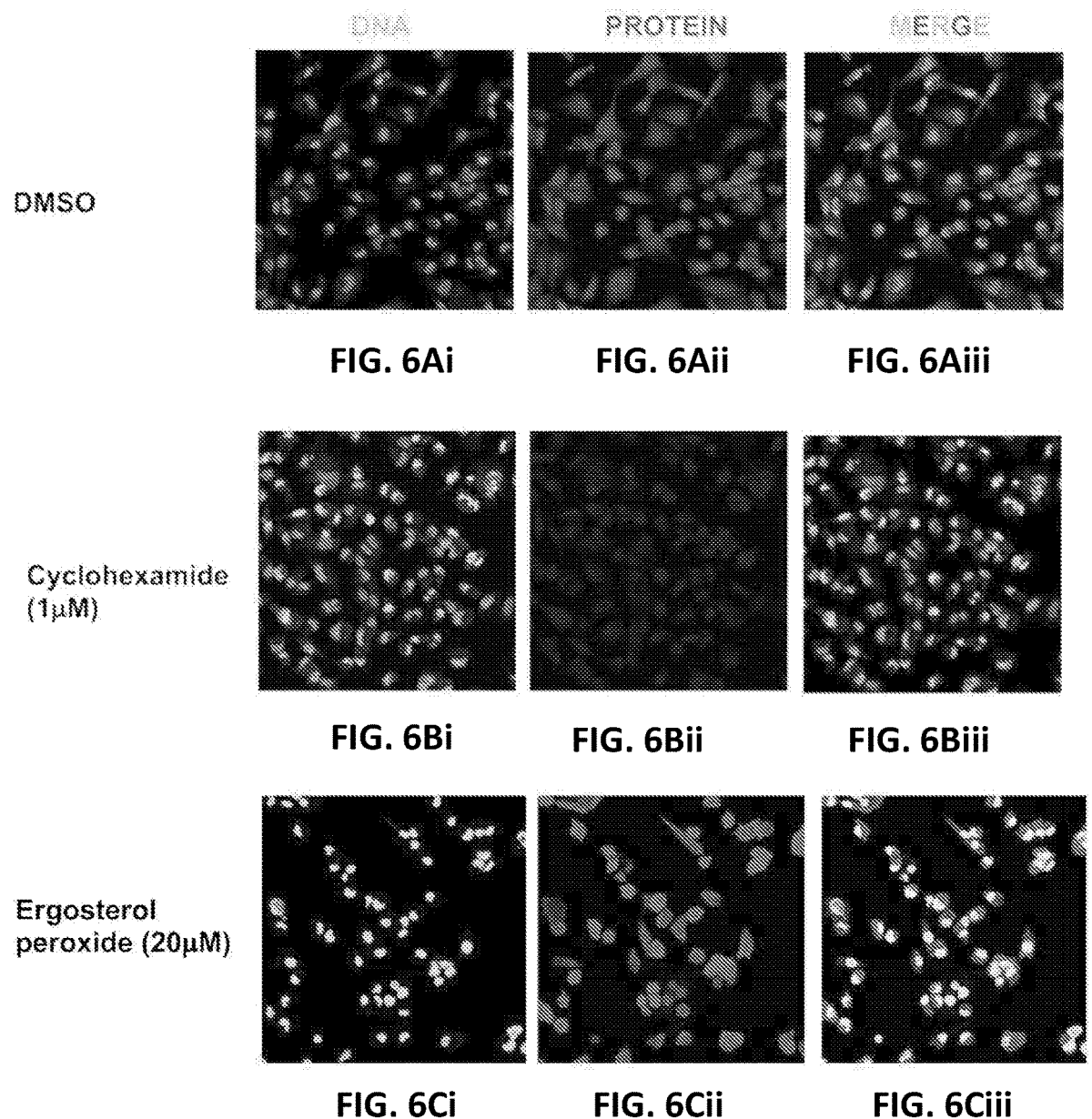

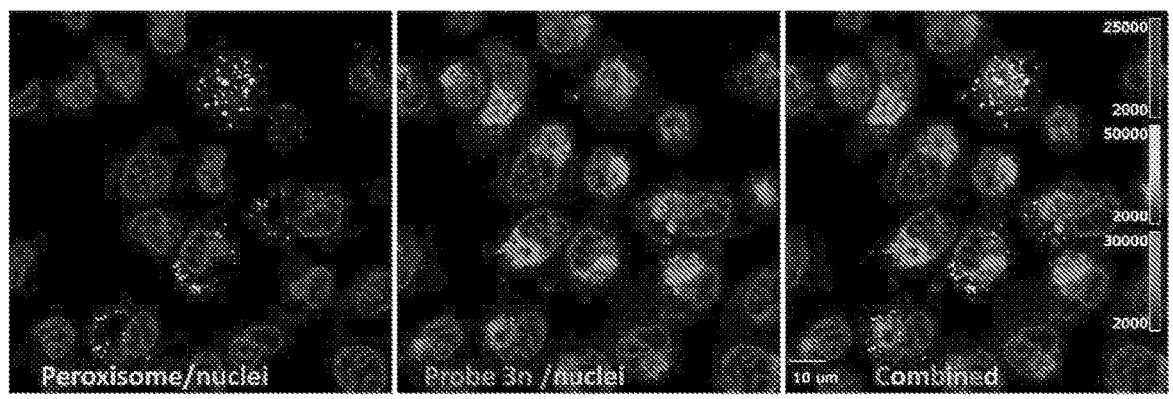
FIG. 17A
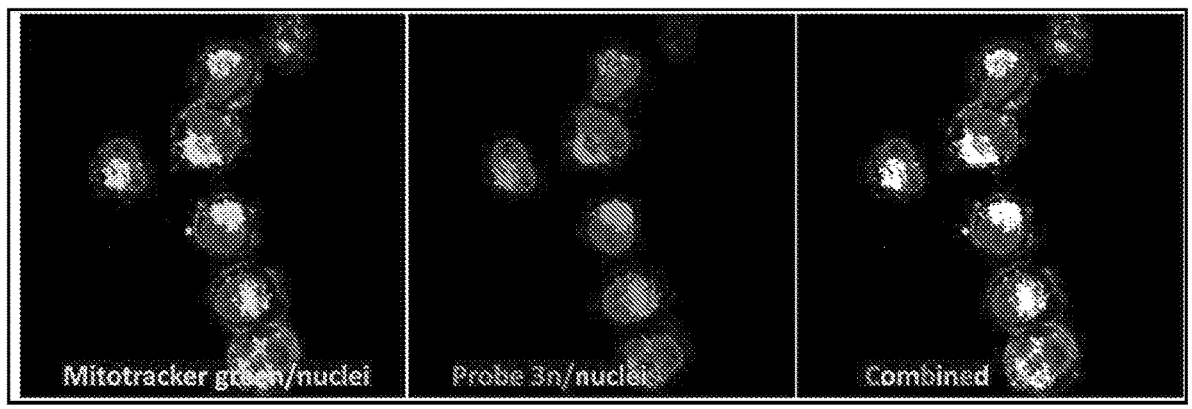
FIG. 17B
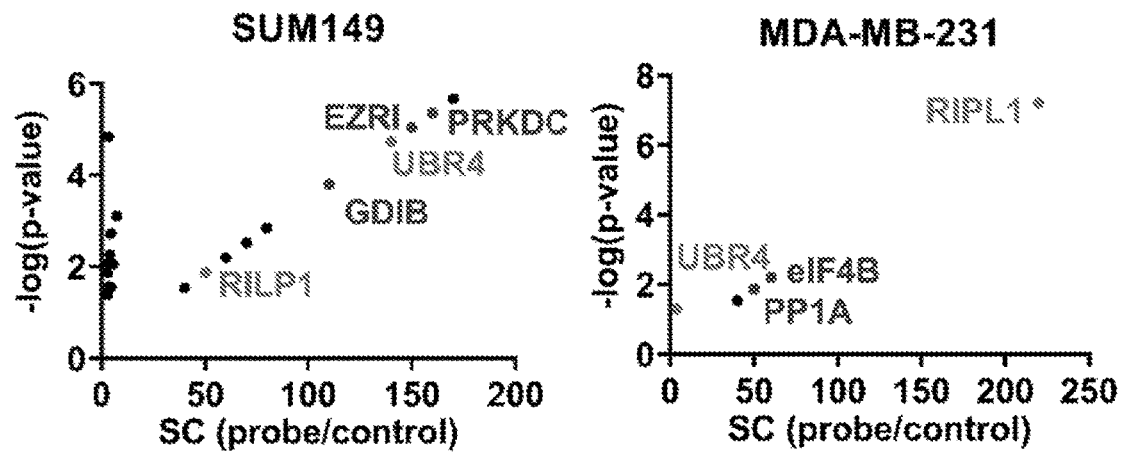
FIG. 18A
FIG. 18B

BIOLOGICALLY ACTIVE GANODERMA LUCIDUM COMPOUNDS AND SYNTHESIS OF ANTICANCER DERIVATIVES; ERGOSTEROL PEROXIDE PROBES FOR CELLULAR LOCALIZATION

RELATED APPLICATIONS

This application is a U.S. nationalization under 35 U.S.C. § 371 of International Application No. PCT/US2020/017053, filed Feb. 6, 2020, which claims the benefit of U.S. Provisional Patent Application Ser. No. 62/802,525 filed Feb. 7, 2019. The disclosures set forth in the referenced applications are incorporated herein by reference in their entireties.

BACKGROUND

Natural products from different sources such as fungi or plants continue to provide hit compounds with anti-cancer potential. Secondary metabolites from GLE include triterpenoids belonging to the ganoderic acid family, sterols (i.e. lanosterol, ergosterol, ergosterol peroxide), lipids, flavonoids, and lignans. The ganoderic acids and the sterols share a similar molecular scaffold with the latter compounds displaying sparse higher oxidation states.

Increased toxic effects from conventional (pharmaceutical) therapies, as well as evidence from recent reports that prove the efficacy of "natural" therapies, have caused a rise in the use of "natural" therapies by patients with cancer. Among these therapies is the whole medicinal mushroom *Ganoderma lucidum*, which has been used in traditional Chinese medicine for more than two millennia. Patients with cancer who take *Ganoderma lucidum* extract (GLE) display improved quality of life and prolonged lives without interference with their conventional therapy. The most common uses for commercially available GLE include prevention and treatment of hypertension, cancer, and immunological disorders. Although the fruiting body of *Ganoderma lucidum* has been used as a traditional medicine for decades, the spores have also become a research subject more recently. The spores contain mainly lanostane-type triterpenes and polysaccharides similar to those found in the fruiting body, which are the main chemical compounds to which anti-cancer activities of GLE are attributed.

Mechanisms of cancer prevention by GLE have been summarized in several reports. Commercially available whole mushroom GLE selectively inhibits breast cancer cell viability and in various models of human cancer induces apoptosis, reduces invasion, and regulates key signaling molecules. Moreover, GLE reduces tumor volume in mice by ~50% when administered alone or in combination with conventional therapy in mice xenografts.

The ergosterol peroxide (EP) natural product (NP) is a compound isolated from plants, algae, lichens, anemonae, corals, and mushrooms such as *Ganoderma lucidum* among others. Ergosterol peroxide has been reported as an antitumor agent, and displays proapoptotic, anti-inflammatory/immunosuppressive effects, anti-mycobacterial, and anti-proliferative activity against cancer cell lines.

The biological activity of an EP rich extract of *Ganoderma lucidum* induces apoptosis in a dose dependent manner against cancer cellular models. EP belongs to the steroidal family of NPs, sharing a cholesterol core with an endoperoxide bridge as the reactive center of the molecule. Although the source of activity presumably arises from this functionality, and several studies have been reported regarding its potential mode of action, the underlying molecular mechanism of EP is not fully understood in cancer.

Triple negative breast cancer (TNBC) is diagnosed when breast cancer cells test negative for the three common types of protein receptors—estrogen, progesterone and hormone epidermal growth factor receptor 2 (HER-2). TNBC is associated with advanced disease stage, higher-grade tumors at diagnosis and is associated with an increased recurrence risk and poor five-year survival rate (relative to other breast cancer subtypes). Most cancer-related deaths are a result of metastasis, and thus the importance of identifying new biological targets for therapy cannot be understated for aggressive cancers such as TNBC.

Mechanistically, metastatic tumor cells are genetically unstable, and in most cancers no single dominant pathway is likely to control metastasis, thus there is a growing interest in developing new pharmacological treatments rising from NPs, which might not affect a single biological target, rather inducing its effects via primary and secondary molecules that cross talk in cancer-dependent signaling pathways. EP has a strong precedence in the literature of targeting several pathways across cancer subtypes. Although there is a unanimous agreement that EP induces cells death in cancer models, the specific biological target (s) remain elusive. Wu and the present inventors have shown that EP induces reactive oxygen species (ROS), which are radicals, with a sole unpaired electron in the outermost shell of electrons. Accordingly, the expression of ROS detoxifying antioxidant proteins is altered in cancer cells in comparison to normal cells. However, ROS display anticancer properties by decreasing cell proliferation, damaging DNA, and inducing apoptosis, among other mechanisms.

Endoperoxides are known for generating radicals. It is hypothesized that homolytic cleavage of the peroxide would take place to generate the expected oxyl radicals, which ultimately leads to the more stable carbon-carbon radical that would presumably bind to specific proteins. Although such reactivity would be expected to be mediated by iron dependency or iron for its mediated action upon co-treatment studies of EP with Iron. EP induces ROS in TNBC cells, but the EP cellular accumulating site, and its specific biological target(s) are unknown.

SUMMARY

The structural elucidation of the most abundant chemical constituents of whole mushroom *Ganoderma lucidum* and their efficacy in treating triple negative inflammatory breast cancer (IBC) is disclosed. IBC is a rare, unique and aggressive subtype of breast cancer that is infrequently studied.

The characteristics and structure of 5,6-dehydroergosterol, a bioactive compound was tested in inflammatory breast cancer (SUM-149) and non-cancerous (BJ) cells. 5,6-dehydroergosterol was purified from *Ganoderma lucidum* extract, and structure is disclosed.

A detailed report is provided of the X-ray crystal of 5,6-dehydroergosterol from *Ganoderma lucidum*.

Ergosterol peroxide (EP) as a single component is the most biologically active compound against IBC models with promising EC50 values in the low micromolar range (SUM-149) and ample therapeutic index in normal cells (BJ, HMEC).

Improved derivatives of GA-01 (GA-01-ME), ergosterol (ergosterol sulfonamide), 5,6-dehydroergosterol (5,6-dehydroergosterol sulfonamide) and EP (EP sulfonamide) were synthesized to improve their solubility.

GA-01, ergosterol, 5,6-dehydroergosterol and EP induce ROS in TNBC and IBC cell models.

Compounds are disclosed that do not affect normal cells while having anti-cancer effects.

Tools (probes) were generated to identify where the compounds co-localize with organelles within the cells.

These chemical tools can be used for live cell imaging studies to delineate the mechanism of action of ergosterol peroxide in cancer cells. A short synthesis route is disclosed to synthesizing ergosterol peroxide probes. These probes accumulate in the cytosol with subcellular specificity.

The biotin-EP probe (3k) was used for target identification through affinity-based proteomic target identification in two TNBC cell lines. Two targets were identified: two potential biological targets, Rab interacting lysosomal protein like 1 (RIPL1) and E3 ubiquitin-protein ligase (UBR4), were identified in both SUM-149 and MDA-MB-231 cell lines. These proteins are known to be distributed across the cytosol and the plasma membrane, which agrees with the co-localisation results. RIPL1 is involved in regulating the cell shape and polarity via cellular protein transport, Although UBR4 is involved in ubiquitination and subsequent degradation of certain proteins, and interacts with the retinoblastoma-associated protein in the nucleus, calcium-bound calmodulin is in the cytoplasm and regulates integrin-mediated signaling.

Ergosterol peroxide conjugates of fluorescent dyes enable live-cell imaging to explore their subcellular interactions. Furthermore, the fluorescent probes were rationally designed to be spectrally orthogonal to organelle-fluorescent trackers for co-localisation studies using fluorescence microscopy.

When possible, commercially available chemical probes for live cell staining organelles (endoplasmic reticulum, mitochondria, and lysosomes) were used. However, to study the Golgi apparatus or peroxisomes, no orthogonal dye was available for the probes. Therefore, transiently transfected with Red Fluorescent Protein (RFP) or Green Fluorescent Protein (GFP) organelle-labelled cellular models were generated. Also, stably transformed cancer cell lines transfected with mRuby-peroxisomes-2 plasmid23b were generated.

Substantial co-localisation was detected with the endoplasmic reticulum using the blue/white endoplasmic reticulum tracker along with probe 3m. Consistent observations were recorded for both MDA-MB-231 and SUM-149 cancer cell lines.

The antiproliferative activity of probe 3m was comparable to that of ergosterol peroxide.

Probe 3n, with a longer linker between the borane core and ergosterol peroxide showed accumulation in the mitochondria.

Chemical modifications of the probes leads to superior potency by causing accumulation in specific organelles to induce greater cellular damage.

Compounds (sulfonamides), tagged probes/esters are considered prodrugs, and are used to overcome the poor solubility of EP. Esters and ketone derivative can't be "obviously predicted by those individuals knowledge of the field" to have improved effects on cancer cells from the parental compound.

The following numbered embodiments (clauses) are contemplated and non-limiting.

1. A method of modifying a cancer-related symptom in a subject, said method comprising the step of administering a pharmaceutical composition comprising a *Ganoderma lucidum* component to the subject, wherein the pharmaceutical composition modifies the cancer-related symptom.

2. The method of clause 1, wherein the modification of the cancer-related symptom is an induction of reactive oxygen species (ROS).

3. The method of clause 1, wherein the modification of the cancer-related symptom is an inhibition of cancer cell viability.

4. The method of clause 1, wherein the modification of the cancer-related symptom is an induction of anti-proliferative activity of cancer cells.

5. The method of clause 1, wherein the modification of the cancer-related symptom is an induction of cell cycle arrest of cancer cells.

6. The method of clause 1, wherein the modification of the cancer-related symptom is an induction of apoptosis of cancer cells.

7. The method of clause 1, wherein the modification of the cancer-related symptom is an induction of PARP cleavage of cancer cells.

8. The method of clause 1, wherein the modification of the cancer-related symptom is an induction of apoptosis of cancer cells.

9. The method of clause 1, wherein the modification of the cancer-related symptom is a decrease in cancer cell migration.

10. The method of clause 1, wherein the modification of the cancer-related symptom is a decrease in cancer cell invasiveness.

11. The method of clause 1, wherein the modification of the cancer-related symptom is a reduction in tumor volume.

12. The method of clause 1, wherein the *Ganoderma lucidum* component is selected from the group consisting of 5,6-dihydroergosterol, ergosterol, ergosterol peroxide, and any combination thereof.

13. The method of clause 1, wherein the *Ganoderma lucidum* component is 5,6-dihydroergosterol.

14. The method of clause 1, wherein the *Ganoderma lucidum* component is ergosterol.

15. The method of clause 1, wherein the *Ganoderma lucidum* component is ergosterol peroxide.

16. The method of clause 1, wherein the *Ganoderma lucidum* component is a *Ganoderma lucidum* derivative.

17. The method of clause 16, wherein the *Ganoderma lucidum* derivative is ergosterol sulfonamide.

18. The method of clause 16, wherein the *Ganoderma lucidum* derivative is 5-6-dihydroergosterol sulfonamide 19. The method of clause 16, wherein the *Ganoderma lucidum* derivative is ergosterol peroxide sulfonamide.

20. The method of clause 1, wherein the *Ganoderma lucidum* component is a compound selected from the group consisting of 3a, 3b, 3c, 3d, 3e, 3f, 3g, 3h, 3i, 3j, 3k, 3l, 3m, and 3n.

21. The method of clause 1, wherein the subject has breast cancer.

22. The method of clause 21, wherein the breast cancer is an inflammatory breast cancer.

23. A method of treating cancer in a subject, said method comprising the step of administering a pharmaceutical composition comprising a *Ganoderma lucidum* component to the subject.

24. The method of clause 23, wherein the cancer is breast cancer.

25. The method of clause 24, wherein the breast cancer is inflammatory breast cancer.

26. The method of clause 23, wherein the *Ganoderma lucidum* component is selected from the group consisting of 5,6-dihydroergosterol, ergosterol, ergosterol peroxide, and any combination thereof.

27. The method of clause 23, wherein the *Ganoderma lucidum* component is 5,6-dihydroergosterol.

28. The method of clause 23, wherein the *Ganoderma lucidum* component is ergosterol.

29. The method of clause 23, wherein the *Ganoderma lucidum* component is ergosterol peroxide.

30. The method of clause 23, wherein the *Ganoderma lucidum* component is a *Ganoderma lucidum* derivative.

31. The method of clause 30, wherein the *Ganoderma lucidum* derivative is ergosterol sulfonamide.

32. The method of clause 30, wherein the *Ganoderma lucidum* derivative is 5-6-dihydroergosterol sulfonamide.

33. The method of clause 30, wherein the *Ganoderma lucidum* derivative is ergosterol peroxide sulfonamide.

34. The method of clause 23, wherein the *Ganoderma lucidum* component is a compound selected from the group consisting of 3a, 3b, 3c, 3d, 3e, 3f, 3g, 3h, 3i, 3j, 3k, 3l, 3m, and 3n.

35. A composition comprising a *Ganoderma lucidum* component and a labeling probe.

36. The composition of clause 35, wherein the *Ganoderma lucidum* component is 5,6-dihydroergosterol.

37. The composition of clause 35, wherein the *Ganoderma lucidum* component is ergosterol.

38. The composition of clause 35, wherein the *Ganoderma lucidum* component is ergosterol peroxide.

39. The composition of clause 35, wherein the *Ganoderma lucidum* component is a *Ganoderma lucidum* derivative.

40. The composition of clause 39, wherein the *Ganoderma lucidum* derivative is ergosterol sulfonamide.

41. The composition of clause 39, wherein the *Ganoderma lucidum* derivative is 5-6-dihydroergosterol sulfonamide.

42. The composition of clause 39, wherein the *Ganoderma lucidum* derivative is ergosterol peroxide sulfonamide.

43. The composition of clause 35, wherein the *Ganoderma lucidum* component is a compound selected from the group consisting of 3a, 3b, 3c, 3d, 3e, 3f, 3g, 3h, 3i, 3j, 3k, 3l, 3m, and 3n.

44. The composition of clause 35, wherein the labeling probe is a fluorescent dye.

45. The composition of clause 44, wherein the fluorescent dye is selected from the group consisting of TAMRA (tetramethylrhodamine), FITC (fluorescein isothiocyanate derivative), and BODIPY (boron-dipyrromethne derivative).

46. The composition of clause 44, wherein the fluorescent dye is TAMRA (tetramethylrhodamine).

47. The composition of clause 44, wherein the fluorescent dye is FITC (fluorescein isothiocyanate derivative).

48. The composition of clause 44, wherein the fluorescent dye is BODIPY (boron-dipyrromethne derivative).

49. The composition of clause 35, wherein the probe is a biotinylated EP used for pull down experiments to identify a target (see FIG. 12).

50. A method of evaluating a biological target in a cell, said method comprising the steps of:
   (a) contacting a composition comprising a *Ganoderma lucidum* component and a labeling probe to the biological target; and
   (b) determining the nature of the labelled target.

51. The method of clause 50, wherein the biological target is an intracellular target.

52. The method of clause 50, wherein the biological target is cytosol.

53. The method of clause 50, wherein the biological target is endoplasmic reticulum (ER).

54. The method of clause 50, wherein the biological target is mitochondria.

55. The method of clause 50, wherein the *Ganoderma lucidum* component is 5,6-dihydroergosterol.

56. The method of clause 50, wherein the *Ganoderma lucidum* component is ergosterol.

57. The method of clause 50, wherein the *Ganoderma lucidum* component is ergosterol peroxide.

58. The method of clause 50, wherein the *Ganoderma lucidum* component is a *Ganoderma lucidum* derivative.

59. The method of clause 58, wherein the *Ganoderma lucidum* derivative is ergosterol sulfonamide.

60. The method of clause 58, wherein the *Ganoderma lucidum* derivative is 5-6-dihydroergosterol sulfonamide.

61. The method of clause 58, wherein the *Ganoderma lucidum* derivative is ergosterol peroxide sulfonamide.

62. The method of clause 58, wherein the *Ganoderma lucidum* component is a compound selected from the group consisting of 3a, 3b, 3c, 3d, 3e, 3f, 3g, 3h, 3i, 3j, 3k, 3l, 3m, and 3n.

63. The method of clause 50, wherein the labeling probe is a fluorescent dye.

64. The method of clause 63, wherein the fluorescent dye is selected from the group consisting of TAMRA (tetramethylrhodamine), FITC (fluorescein isothiocyanate derivative), and BODIPY (boron-dipyrromethne derivative).

65. The method of clause 63, wherein the fluorescent dye is TAMRA (tetramethylrhodamine).

66. The method of clause 63, wherein the fluorescent dye is FITC (fluorescein isothiocyanate derivative).

67. The method of clause 63, wherein the fluorescent dye is BODIPY (boron-dipyrromethne derivative).

BRIEF DESCRIPTION OF THE DRAWINGS

FIG. 2A. Ergosterol.

FIG. 3A. GA-01 had an $EC_{50}>50$ μM in various breast cancer cell lines; FIG. 3B. Ergosterol, and 5,6-dihydroergosterol had an $EC_{50}>50$ μM, and ergosterol significantly reduced SUM-149 cell viability at 64 μM; FIG. 3C. BJ cell viability was not affected by the compounds at the concentrations tested. Bars represent mean±SEM of at least 3 biological replicates. **$P<0.01$ compared to vehicle.

FIG. 4A., 4B. SUM-149 cells treated with EP for 24 h significantly decreased cell viability.

FIG. 5A., P1=vehicle, P2=EP (20 µM); A cell-cycle progression assay of cells treated with EP for 48 h shows an increased percentage of cells in G1 and decreased percentage of cells in G2/M; FIG. 5E. SUM-149 cells.

FIG. 6A.-6C. Click assay showing effects of EP on de novo protein synthesis in MDA-MB-231 breast cancer cells; FIG. 6A.i, 6Aii, 6Aiii; DMSO; FIG. 6B. i, 6Bii, 6Biii, cycloheximide (1 µM); FIG. 6C. i, 6Cii, 6Ciii, EP, 20 µM, 2 h.; i=DNA stain (green); ii=New protein (red); iii=Merge (20×).

FIG. 7A. MDA-MB-231 breast cancer cells or FIG. 7B. SUM-149 breast cancer cells were treated as described in the Materials and Methods section with EP (20 µM), or menadione (10 µM) as a positive control; N-Acetyl Cysteine (500 µM) was added to inhibit ROS formation; Bars depict mean±SEM of triplicates. **P<0.0001, *P<0.001 compared to vehicle. ####P<0.0001 compared to NAC.

FIG. 8A. EP decreases cancer cell migration.

FIGS. 11-15. relate to Ergosterol peroxide (EP) analogues and probes.

FIG. 11. shows synthesis of EP and its analogues.

FIG. 12. relates EP analogues (3a-3k).

FIGS. 13A-13C. Transient and stable organelle-labelled MDA-MB-231; FIG. 13A. Transiently transfected GFP fused to the peroxisomal C-terminal targeting sequence cells with nuclear blue stain; FIG. 13B. Transiently transfected RFP fused to Golgi apparatus resident enzyme N-acetyl galactaminyl transferase cells with nuclear blue stain; FIG. 13C. Stable mRuby-peroxisomal targeting signal 1 cells.

FIG. 14A. Peroxisome.

FIGS. 15A-15C. Regents and conditions for syntheses of 3l-3n probes; FIG. 15A. 1. (a) PyBOP, DMSO, Hünig's base, 25° C., (b) sodium ascorbate (0.2 eq), CuSO$_4$, 7H$_2$O (0.1 eq), t-BuOH:H$_2$O-1:1 (viv); FIG. 15B. (a) 2,4,6-trichloro-benzoyl chloride, Et$_3$N, 25° C., CH$_2$Cl$_2$, 1 hr. 2. (b) EP, DMAP, CH$_2$Cl$_2$, 25° C., 10 hr; FIG. 15C. (a) BDY 630-X-NHS, EP, Et$_3$N, 25° C., CH$_2$Cl$_2$.

FIG. 16A. Fluorescent intravital image analysis of primary tumor starting from injection day (week 1). Treatment [vehicle or ergosterol peroxide (EP) i.p. administered three times per week] started on week 6 (red square). Image shows tumor progression of one representative mouse out of 8 per treatment group.

FIG. 17A.-17B. Evaluation of probe 3n; FIG. 17A. cell light peroxisome-GFP/MDA-MB-231; FIG. 17B. MitoTracker Green and 3n.

FIG. 18A.-18B. Scatter plots displaying potential protein targets of 3k, Spectral Counts (SC) against p-values. FIG. 18A. SUM-149; FIG. 18B. MDA-MB-231.

FIG. 19A. no fluorescence of the control compound is observed after washing.

FIG. 20A. transiently transfected Golgi-RFP SUM-149 cells.

DETAILED DESCRIPTION

Figure 1:
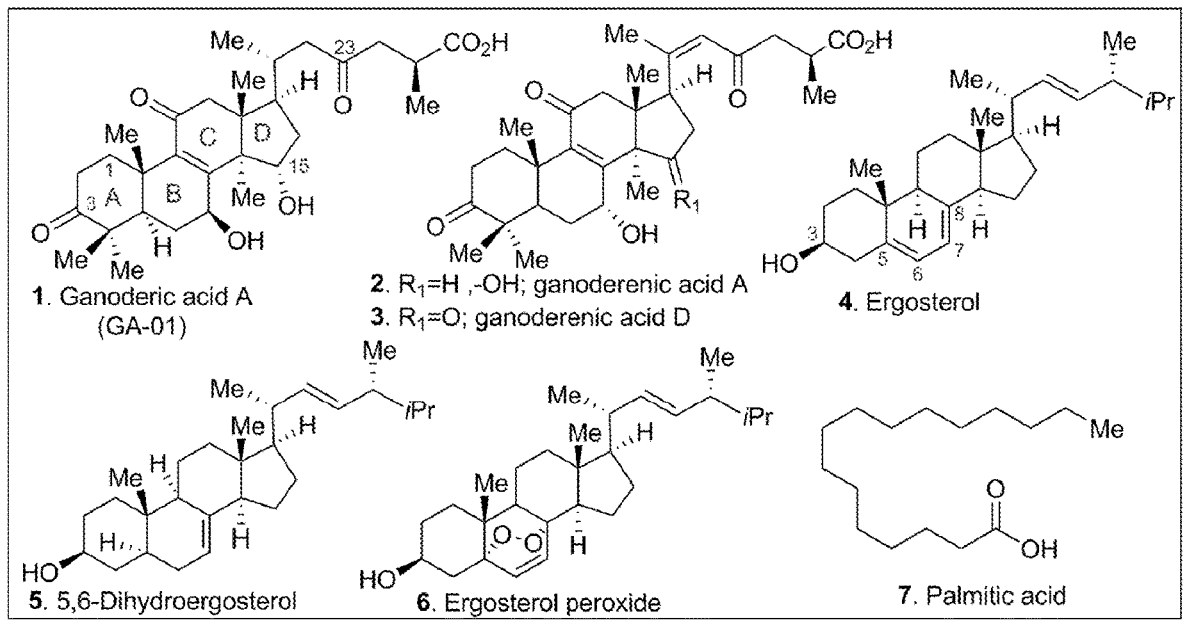
FIG. 1. Selected chemical constituents of GLE; Compounds extracted from *Ganoderma lucidum* include 1. ganoderic acid A, 2-3. ganoderenic acid A and D, 4. ergosterol, 5. 5, 6-dihydroergosterol, 6. ergosterol peroxide, and 7. palmitic acid.

The present disclosure relates the chemical constituents of GLE responsible for its biological activity and characterizes their efficacy as single agents in various cancer cell models, particularly in inflammatory breast cancer. Herein the structures of the 7 most abundant chemical components of GLE (whole mushroom ReishiMax®) by NMR studies, X-ray crystallography and analogue derivatization are disclosed. The in vitro efficacy of these compounds, which include triterpenes, and sterols, is demonstrated in various cancer models. To overcome poor solubility properties, improved derivatives were synthesized which display superior potency against aggressive models of breast cancer.

Compounds that were modified and so do not exist in nature, include sulfonamide derivatives. All derivatives, including EP were synthetically engineered.

Three of the seven compounds (ergosterol, 5,6-dehydroergosterol and ergosterol peroxide) exhibited significant in vitro anticancer activities. In TNBC/IBC cells ergosterol peroxide (EP) displays anti-proliferative effects through G1 phase cell cycle arrest, apoptosis induction via caspase 3/7 activation, and PARP cleavage. EP decreased migratory and invasive effects of cancer cells while inhibiting the expression of total AKT1, AKT2, BCL-XL, Cyclin D1 and c-Myc in the tested IBC cells. These compounds induce reactive oxygen species, compromising cell fate. Furthermore, a superior derivative, ergosterol peroxide sulfonamide was generated. This compound has improved potency in IBC cells and ample therapeutic index (TI>10) compared to normal cells. The combined studies indicate that EP from *Ganoderma lucidum* extract is a promising molecular scaffold for further exploration as an anti-cancer agent. Previous reports show *Ganoderma lucidum* extract (GLE) demonstrated significant anticancer activity against triple negative inflammatory breast cancer models. Herein, the bioactive compounds of GLE responsible for this anticancer activity were identified.

The rationale behind the use of prodrugs was to optimize the absorption, distribution, metabolism, excretion, and unwanted toxicity of the parent compounds. The choice of sulfonamides was not an obvious approach to overcome solubility properties, but internal information on the properties of such compounds were discovered in cell models.

Compounds with anti-cancer activities that have minimal effects on normal cells and serve as potential therapies for aggressive malignancies such as triple negative and inflammatory breast cancers, are disclosed. Patients that have aggressive tumors are expected to especially benefit from this discovery. Also, tool compounds were generated for the organelle identification of the compounds.

Characteristics and the structure of 5,6-dehydroergosterol, a bioactive compound tested in breast cancer (SUM-149) and normal (BJ) cells, are disclosed. Improved derivatives include Ganoderic acid A—methyl ester, Ergosterol sulfonamide, 5,6-dihydroergosterol sulfonamide, and EP sulfonamide. 5,6-dehydroergosterol was purified from *Ganoderma lucidum* extract and its chemical structure is provided. Ergosterol peroxide (EP) organelle localization and efficacy against solid and blood tumors is demonstrated. The compounds described herein do not affect normal cells, while having anti-cancer effects.

Elucidation of the structures of the most abundant chemical constituents of whole mushroom *Ganoderma lucidum* was done and their efficacy in cancer models tested. The isolated compounds of GLE display biological activity across multiple cancer cell lines, with several degrees of potency. The results here demonstrate for the first time: i) that EP as a single component of GLE, is the most biologically active compound against aggressive inflammatory breast cancer models, with promising EC50 values in the low micromolar range, and ample therapeutic indices in normal cells; ii) the X-ray crystal of 5,6-dehydroergosterol from *Ganoderma lucidum*; and iii) that improved derivatives of GA-01, ergosterol, 5,6-dehydroergosterol and EP addressed by their solubility were developed. Unlike many natural products, GA-01 and EP, do not act on cellular proliferation by inhibiting protein synthesis. Rather cell death is mediated by caspase activation through the modulation of cancer dependent mechanisms (e.g. AKT pro-survival pathway). The data indicates that GA-01, ergosterol, 5,6-dehydroergosterol and EP induced ROS in breast cancer cell models, suggesting that ROS mediated-mechanisms contribute in the onset of cell death signaling pathways. To better understand the cascade of signaling events, results demonstrate that EP modulates AKT, with subsequent reduction of proteins involved in cancer cell survival, proliferation, and progression (e.g. Cyclin D1, c-Myc). Finally, more potent compounds, such as EP sulfonamide were developed.

Ergosterol peroxide (EP) selectively displays cytotoxicity against a wide range of diseases. However, its mode of action remains unknown. Efficient synthesis of EP provided access to chemical probes for live cell studies and proteomic profiling. The EP analogues show promising anti-proliferation activity against breast cancer cell models, providing information on the structure-activity-relationship of this natural product to develop superior analogues. Present results herein demonstrate that EP is distributed across the cytosol with significant accumulation in the ER of cancer cell lines. Also, these EP chemical tools enable the discovery of its potential biological target(s) in breast cancer cell lines.

Efforts to address the specific target in breast cancer cellular models are disclosed. Thus, in the present disclosure, the EP-chemical probes were generated to study subcellular co-localization in order to recover its potential mechanism in breast cancer cell models. An efficient synthetic approach to EP and its analogues from ergosterol was developed. The resultant EP compounds were evaluated for cytotoxicity/apoptosis via CellTiterGlo assay, and propidium iodide assay.

The synthesis of EP probes was performed to evaluate potential biological target(s). The EP analogues provided information regarding structure-activity-relationship, aiding in the development of improved ergosterol peroxide derivatives. These chemical tools are useful for live cellular studies across cell lines and to delineate the exact mechanism of action of EP in cancer cells, rendering these chemical probes an ideal molecular scaffold for potential anticancer agents. A short synthesis of EP probes for live cell studies was disclosed. EP was found distributed across the cytosol with significant accumulation in the ER. EP probes show promising anti-proliferation activity against solid tumour cell models, providing information on the structure-activity-relationship and potential biological targets of this natural product.

The constructed probes appear to use "routine chemistry," synthesis of the fluorescent probes via esterification of EP with a Bodipy chromophore as the source of fluorescence. However, the present approach strategically reduced the size of the linker to minimize potential effects of the Bodipy tag (influencing the cellular accumulation of EP in the cell). Results include the generation of the corresponding Bodipy tag controls to demonstrate that the probes were not directed by this fluorescent tag. The corresponding cellular models (stably and transiently transfected) were generated to be orthogonal to the fluorescent probes making the approach unique and not routine. The results obtained indicate that EP accumulates in the ER and the cytosol. This narrows down the potential targets in the cell because ergosterol, the parental source of EP in nature can integrate itself across the membranes of the cell including internal organelle membranes.

GLE Chemical Constituents

Most mushrooms contain about 90% water by weight, and the remaining 10% consists of protein, fat, carbohydrate, fiber, vitamins, and minerals. Medicinal mushrooms such as *Ganoderma lucidum* also contain a variety of bioactive molecules, namely triterpenes, steroids, phenols, nucleotides, glycoproteins, and polysaccharides. Triterpenes, polysaccharides, and peptidoglycans are the 3 major physiologically active constituents in *Ganoderma lucidum*. Initial screening revealed that only a few fractions induced selective cell death in cancer cell lines. However, additional unidentified compounds in the fractions at minute quantities might also possess anti-cancer activity or interact synergistically with the identified compounds. For those initial screenings, the total anti-cancer activity of each fraction (i.e. fraction A-F), rather than the anti-cancer activity of a single molecule was monitored. Further characterization and purification of the bioactive components yielded several abundant compounds from a total of 100 fractions. GLE was extracted via Soxhlet extractor for 24 h in isopropanol (1 mL/10 mg). Bioassay-guided fractionation of the crude extract indicated the presence of tetracyclic triterpenes from ganoderic acid and ergosterol (compounds 1-6) series (by TLC and MS) and lipids (compound 7).

Figure 9:
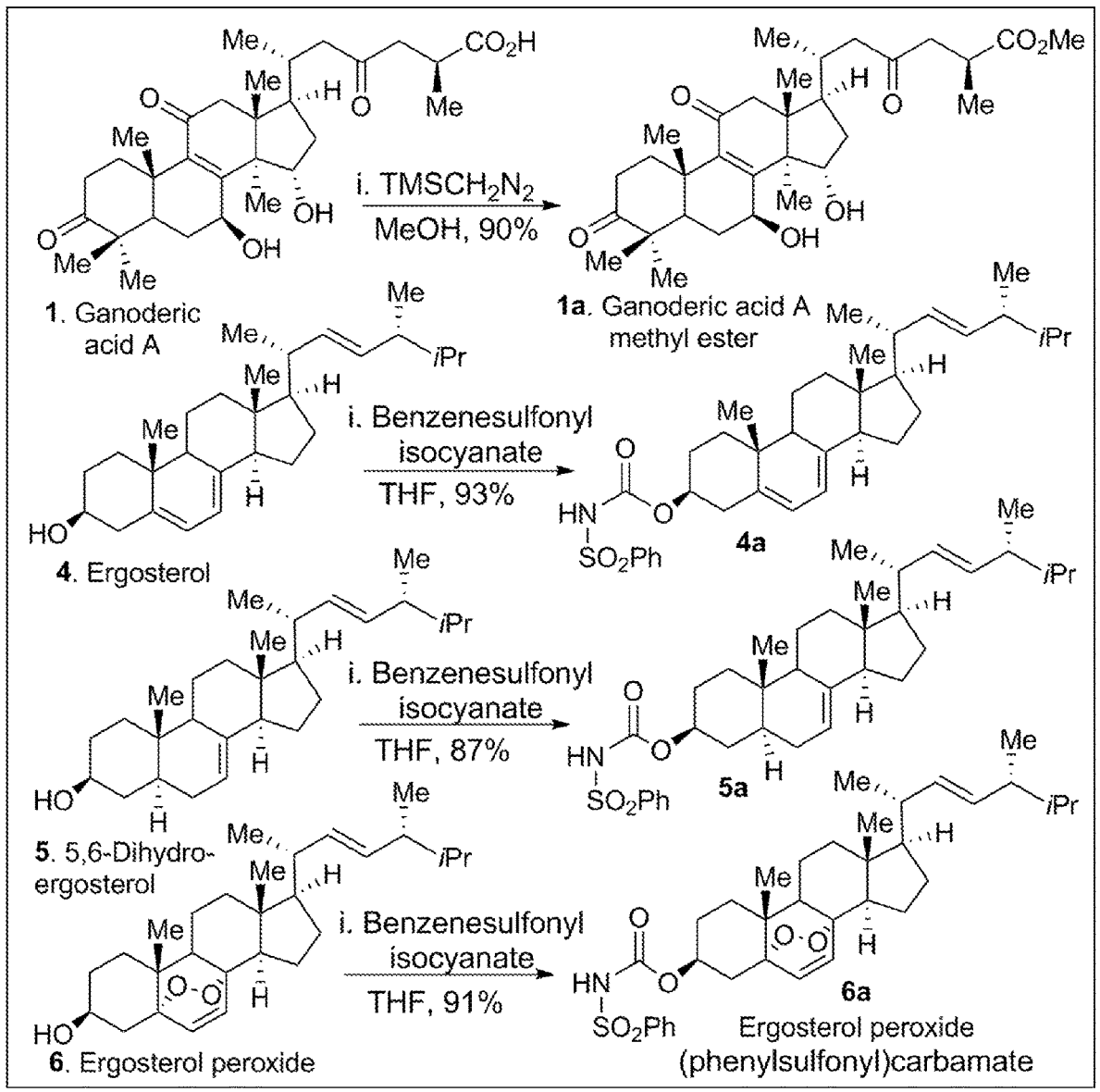
FIG. 9. Chemical transformations of GA-01, ergosterol, 5,6-dihydroergosterol and ergosterol peroxide to GA-01-ME (compound 1a), ergosterol sulfonamide (compound 4a), 5,6-dihydroergosterol sulfonamide (compound 5a) and ergosterol peroxide sulfonamide (compound 6a).

Further characterization of compounds 1-7 (FIG. 1) revealed that palmitic acid (compound 7) was the most abundant compound in the extract by weight. Although these compounds are reported in the literature, their purification poses challenges, particularly for the ganoderic acids, which share similar retention times. In fact, to obtain pure ganoderic acid A (GA-01, compound 1), it was necessary to resort to generating the methyl ester of ganoderic acid A (GA-01-ME) (see FIG. 9, compound 1a), which could be easily separated from the unidentified compounds. Hydrolysis of the methyl ester with base provided GA-01 as an amorphous solid, in agreement with reported characterization data. Ganoderenic acid A and Ganoderenic acid D (compounds 2-3, respectively) were isolated in minute quantities because they overlap with other isomers, co-eluted in the silica gel column, and did not yield enough material for subsequent biological studies. Repeated column chromatography provided 3 sterols; their spectroscopic properties ($^1$H- and $^{13}$C-NMR) confirmed that they were ergosterol (compound 4), 5,6-dehydroergosterol (compound 5), and ergosterol peroxide (compound 6), see FIG. 1.

Figure 2A:
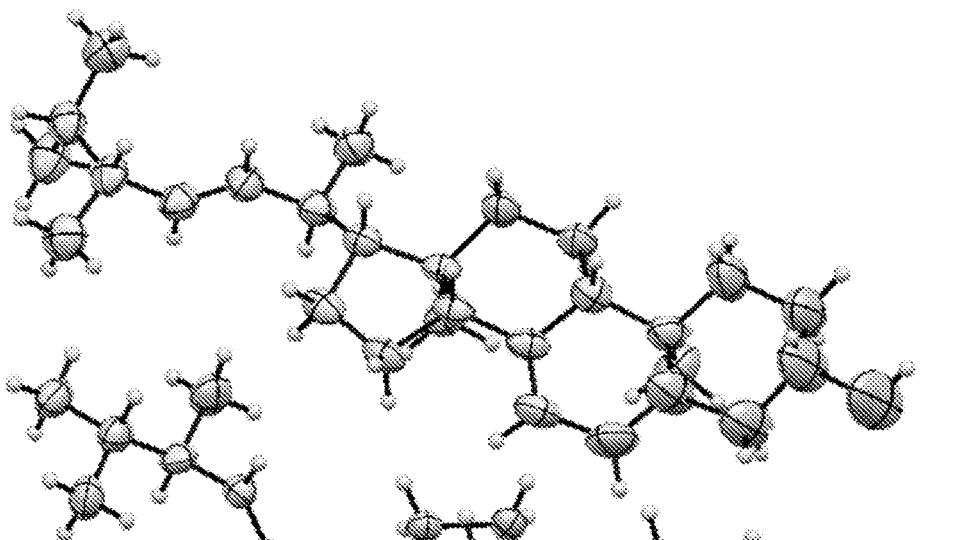
FIG. 2A.-2B. ORTEP structures.
Figure 2B:
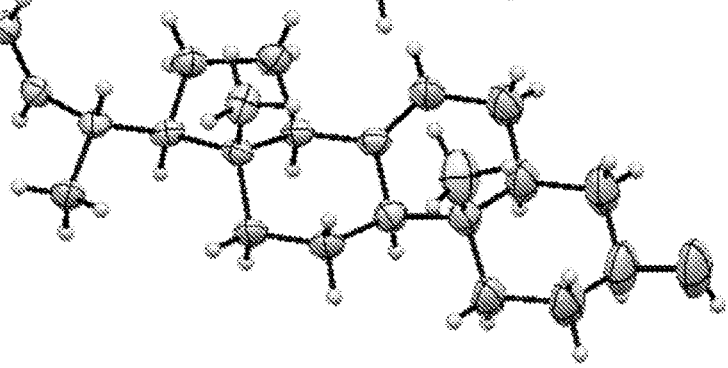
FIG. 2B. 5,6-dihydroergosterol.

Ergosterol is the major fungal membrane sterol that regulates fluidity and plasma membrane biogenesis and function. Importantly, the structures of ergosterol and 5-6-dihydroergosterol were further confirmed by subjecting them to X-ray crystallography. Although several X-ray crystal structures have been reported for ergosterol, the results described herein report the X-ray structure of 5-6-dihydroergosterol, which has not been previously reported. The ORTEP structures of the dimeric unit cell are depicted in FIG. 2; ball-and-stick representations of the X-ray molecular structures are shown in Crystallographic data were summarized by detailed parameters.

The structural elucidation of ergosterol peroxide (EP, compound 6), the most biologically active compound, was confirmed by mass spectrometry coupled with 2D NMR experiments, namely COSY ($^1$H-$^1$H correlation), HMQC ($^1$H-$^{13}$C correlation), HMBC ($^1$H-$^{13}$C correlations), and NOESY, which identified the structure as ergosterol peroxide (EP). Both physical and spectroscopic data of EP are in full agreement with other data previously reported for ergosterol peroxide.

EXAMPLES

Examples are provided for illustrative purposes and are not intended to limit the scope of the disclosure.

Example 1: Effects of GLE Compounds on Cancer Cells In Vitro

GLE Chemical Constituents Decrease Cancer Cell Viability

To investigate whether purified GLE compounds exert anti-cancer activities, cell viability assays were performed in breast cancer (MDA-MB-231 and MCF-7) and inflammatory breast cancer (IBC, SUM-149 and SUM-190) models. The compounds' activity was also evaluated in human and murine leukemia (KOPN8, BCR-ABL, UoCB-1, SUP-B15, NALM06) cell lines. As a control, normal human skin fibroblasts (BJ) cells and non-cancerous mammary epithelial cells (MCF10A) were used.

Figure 3A:
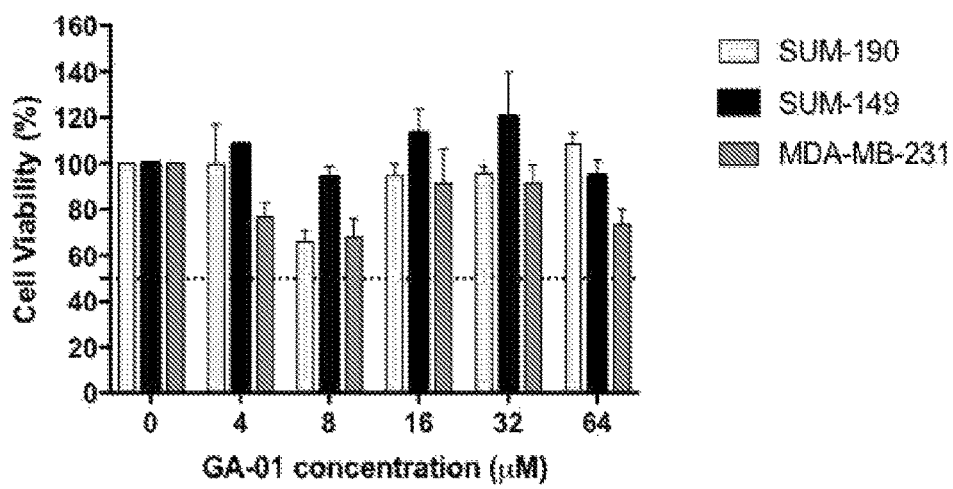
FIGS. 3A-3C. Effect of GA-01, ergosterol, 5,6-dihydroergosterol, and ergosterol peroxide in breast cancer cell lines and normal fibroblasts; SUM-149, MDA-MB-231, SUM-190, and BJ cells were seeded and treated as described in the Materials and Methods section.
Figure 3B:
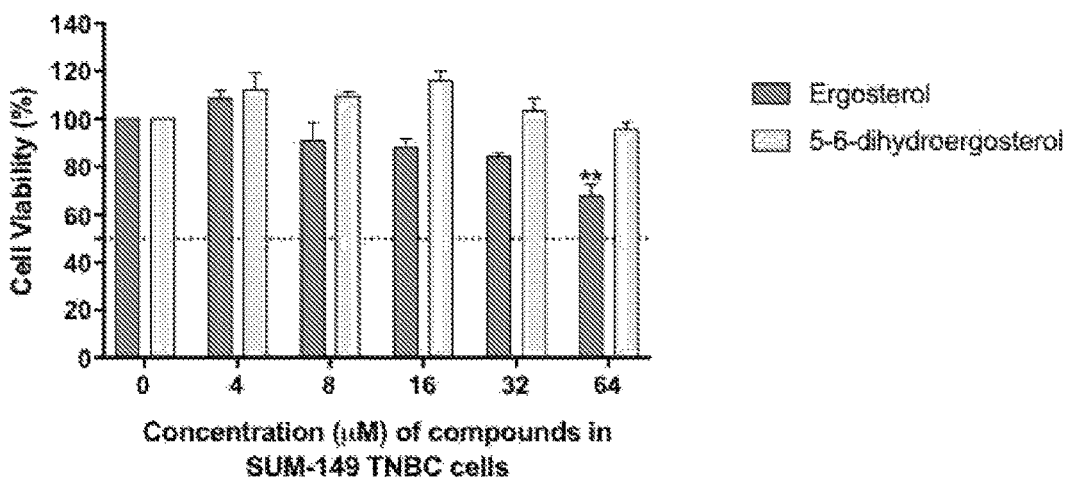
Figure 3C:
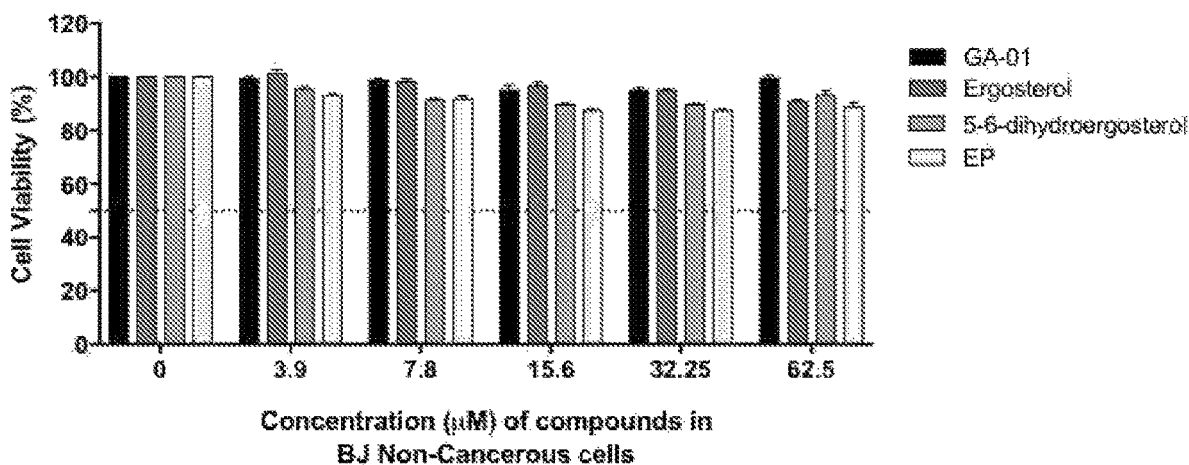

Different concentrations of GLE-extracted bioactive chemical components were tested for 72-h treatment periods. Dose-dependent studies of the identified GLE-extracted chemical components using CellTiter-Glo or PI staining viability assays showed modest activity of GA-01 and 5-6-dihydroergosterol. Their efficacy is at the higher micromolar range (>50 μM) for various breast cancer cell lines (FIG. 3A) under the tested conditions. Ergosterol significantly reduced cancer cell viability starting at 64 μM in breast cancer cellular models (FIG. 3B). Importantly, GA-01, 5,6-dehydroergosterol, ergosterol or EP did not induce cytotoxic effects in normal BJ cells (FIG. 3C). Moreover, palmitic acid did not show activity at the tested concentrations in the evaluated cell lines.

Figure 4A:
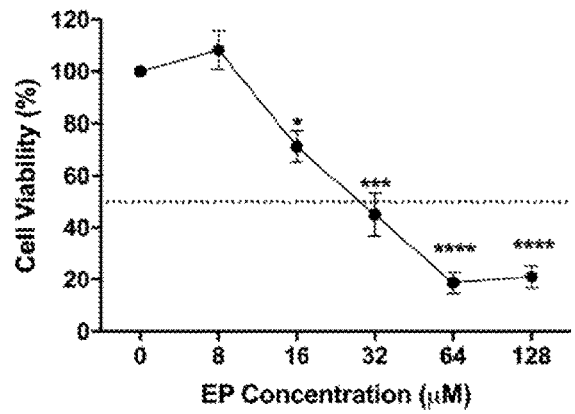
FIG. 4A.-4E. Effect of ergosterol peroxide (EP) in breast cancer cell lines; SUM-149, MDA-MB-231, and SUM-190 cells were seeded and treated as described in the Materials and Methods section.
Figure 4B:
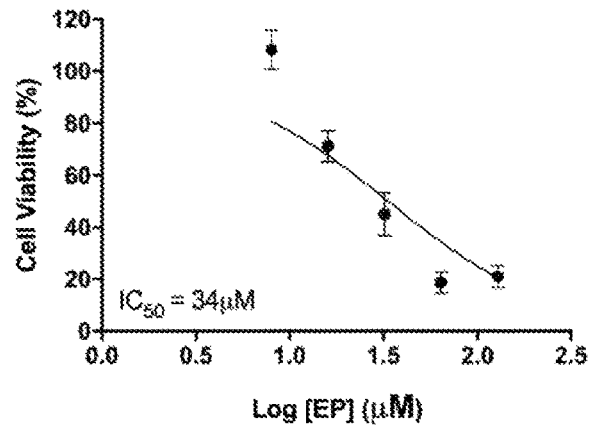
FIG. 4C., 4D. Treatment with EP for 72 h significantly reduced SUM-149 cell viability beginning at 8 μM, EC50=20 μM.
FIG. 4E. Comparison of SUM-149, MDA-MB-231, and SUM-190 cell viability after treatment with EP shows reduced viability in all breast cancer cells; Bars represent mean±SEM of at least 3 biological replicates. *P<0.05, P<0.01, *P<0.001, ****P<0.0001 compared to vehicle.
Figure 4C:
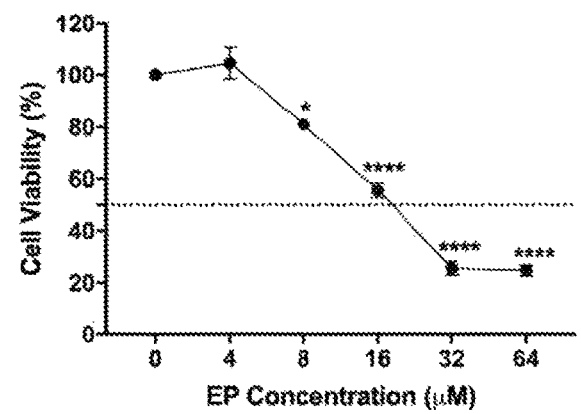
Figure 4D:
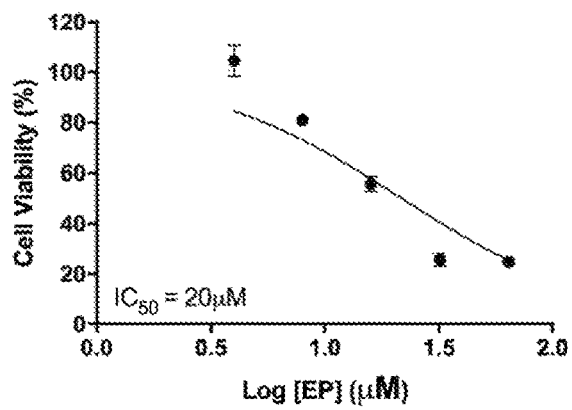
Figure 4E:
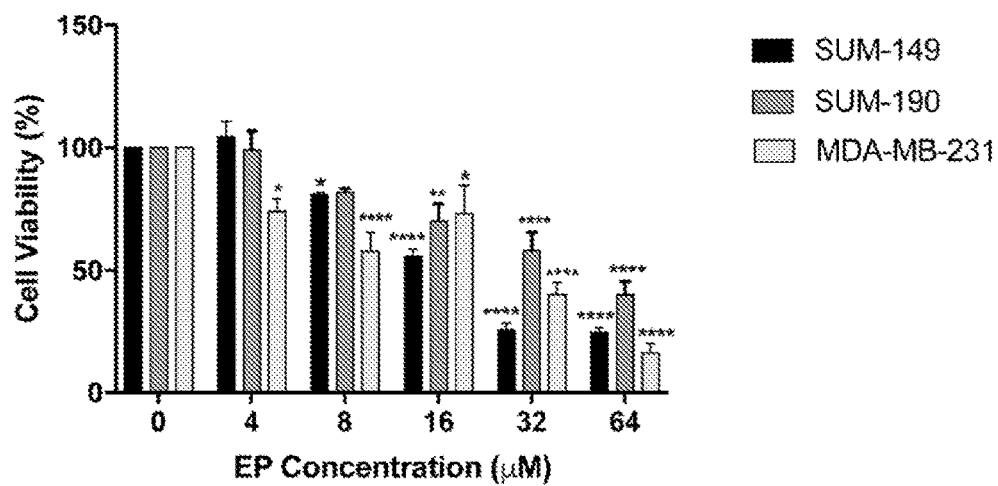

From the seven isolated bioactive compounds, EP showed the greatest anti-cancer activity. For the first time it was demonstrated that EP induces a time- and concentration-dependent decrease (P<0.05) in SUM-149 TNBC/IBC cell viability, with reported $EC_{50}$ values of 34 μM and 20 μM at 24 and 72 h, respectively (FIG. 4A-D). Moreover, these results for MDA-MB-231 TNBC cells and SUM-190 IBC cells also show inhibition of viability by EP in a concentration-dependent manner, with the $EC_{50}$ being 19 μM and 43 μM, respectively (FIG. 4E). These results suggest that TNBC cells might display higher sensitivity to EP. SUM-149 cell number was reduced, while morphology was affected, and the presence of vacuoles was detected upon EP treatment. EP also displayed reduced viabilities, with reported $EC_{50}$ values ranging from 7 μM to 22 μM in additional cancer cellular models, whereas in normal human fibroblast BJ cells (FIG. 3C) and MCF10A non-cancerous mammary epithelial cells, EP did not induce cytotoxicity. Therefore, EP exerts selective effects on cancer cell viability, similar to the effects obtained with whole mushroom extract (GLE), indicating an ample therapeutic window for this compound.

EP Induces Cell Cycle Arrest and Apoptosis

Figure 5A:
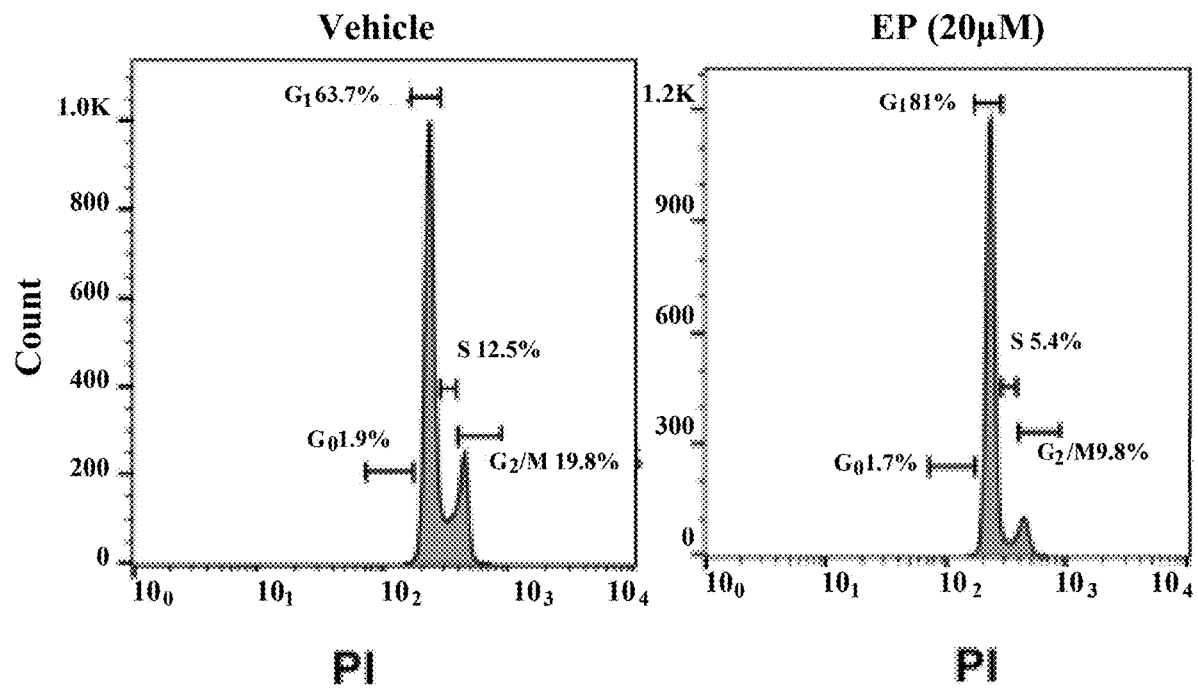
FIG. 5A.-5G. Effect of EP on SUM-149 breast cancer cells.

To determine whether the inhibition of cell viability induced by EP was due to effects on cell-cycle progression, the compound's effects in SUM-149 TNBC/IBC cells were investigated. Results show a significant effect of EP on cell-cycle stage in SUM-149 cells (FIG. 5A). Specifically, a significant (P<0.001) increase in percentage of cells (~20%)

in G1 phase was detected, with a significant reduction (P<0.05) of the percentage of cells (10%) in G2/M, indicative of an arrest in G1.

Figure 5B:
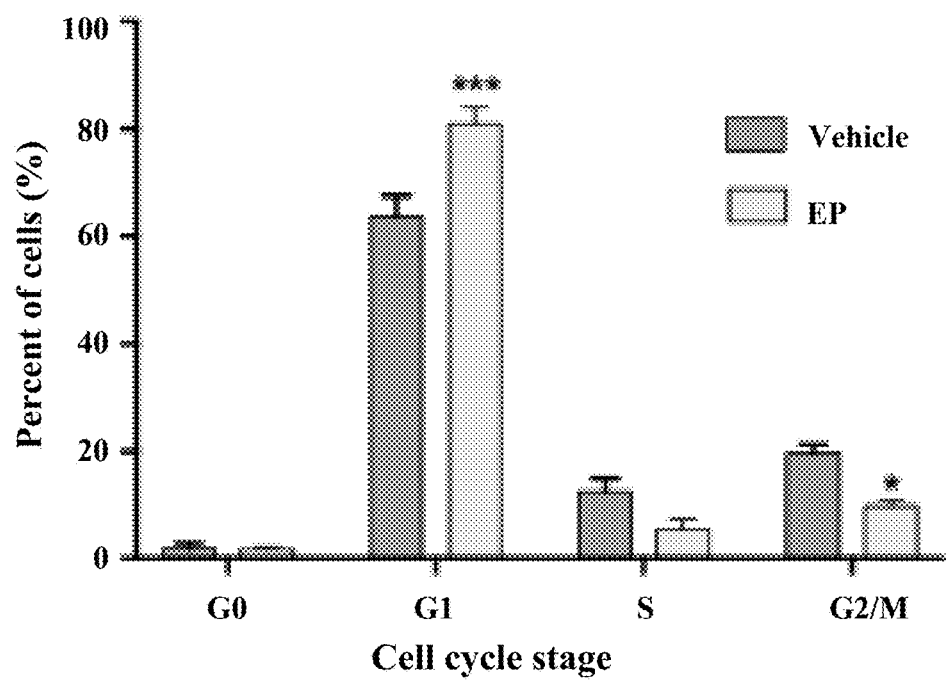
FIG. 5B. graphical results of FIG. 5A.
Figure 5C:
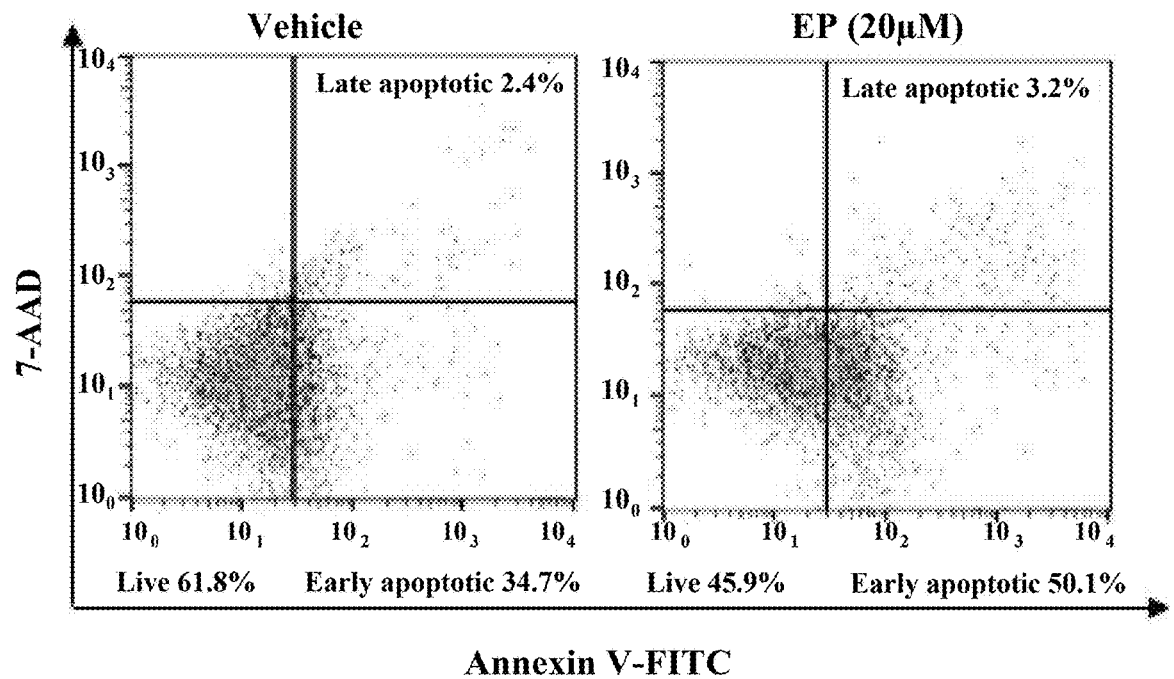
FIG. 5C. Cell death assay shows decreased live cells and an increased percentage of cells in early apoptosis after 48 h of EP treatment.
Figure 5D:
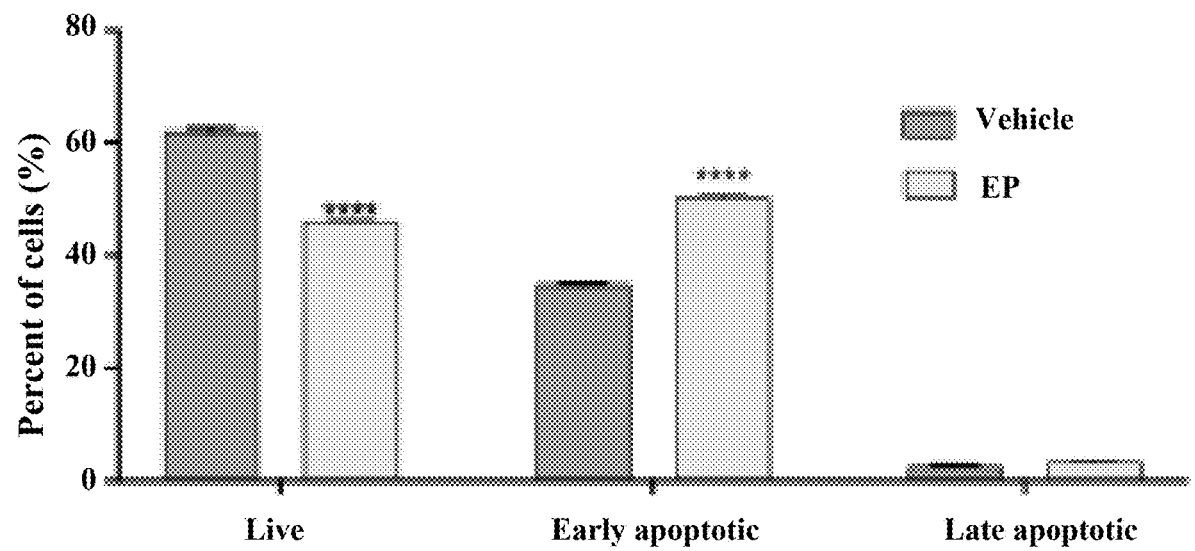
FIG. 5D. Graphs show that EP decreases viability and increases apoptotic activity.
Figure 5E:
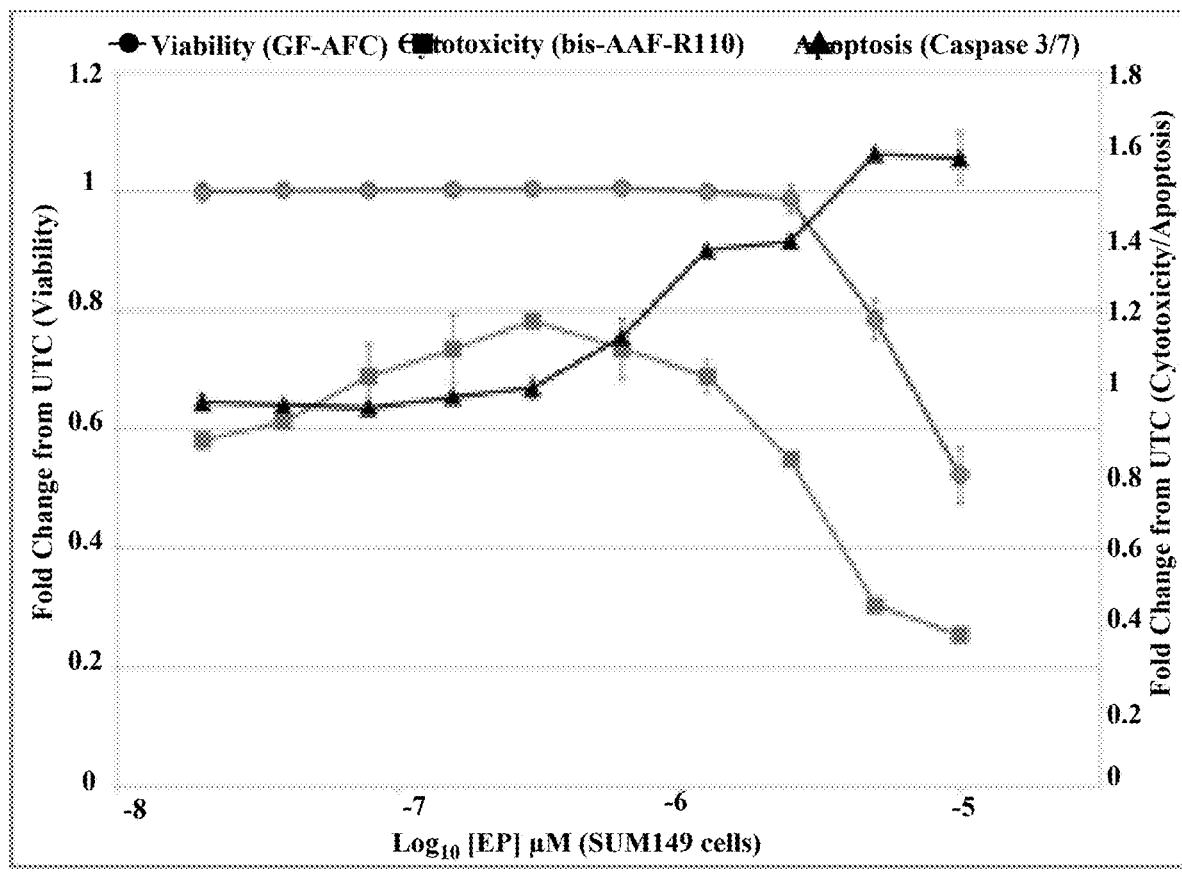
FIG. 5E.-5F. EP induces apoptosis via caspase 3/7 activity in breast cancer cells; The Triplex Glo assay was used to determine viable cells (GF-AFC, closed gray circles), compound cytotoxicity by membrane integrity (bis-AAF-RF110, closed gray squares) or apoptotic cells (caspase 3/7 activity, black triangles)
Figure 5F:
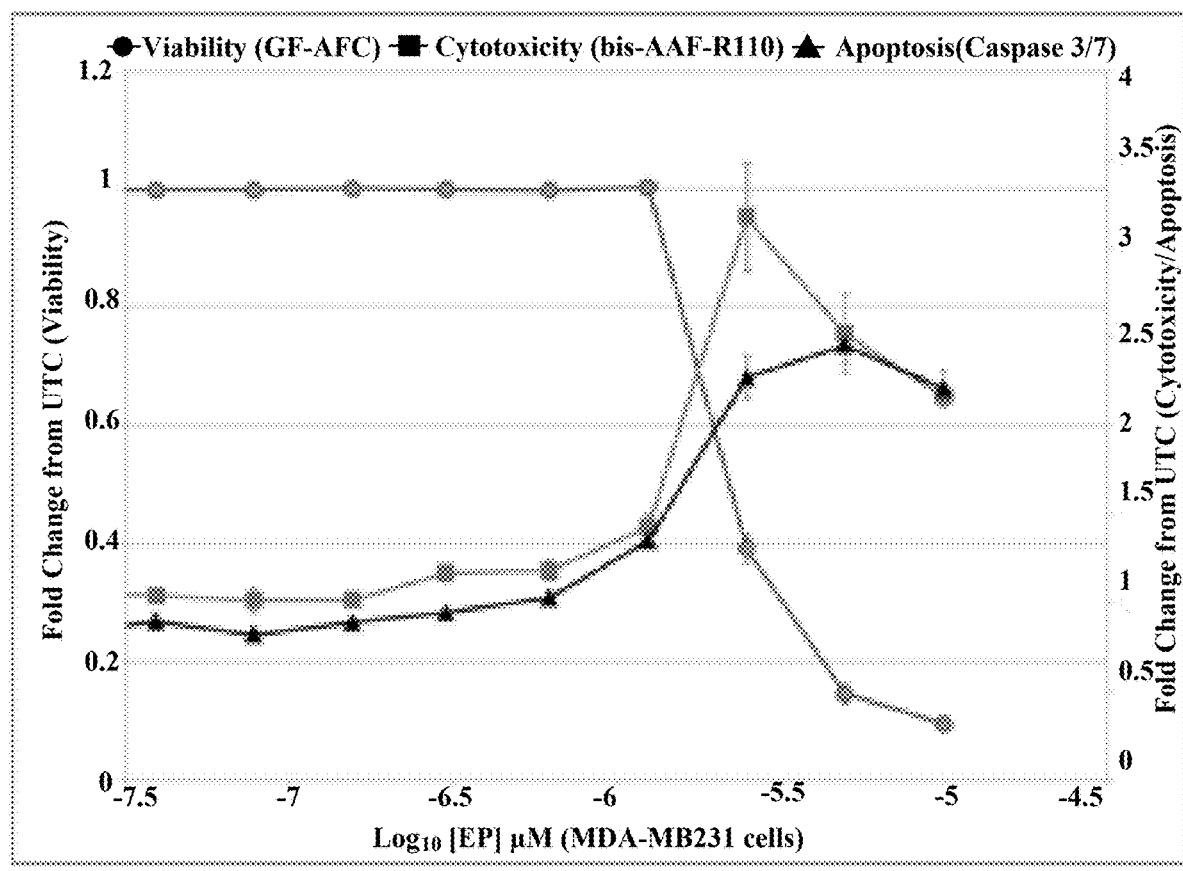
FIG. 5F. MDA-MB-231 cells.
Figure 5G:
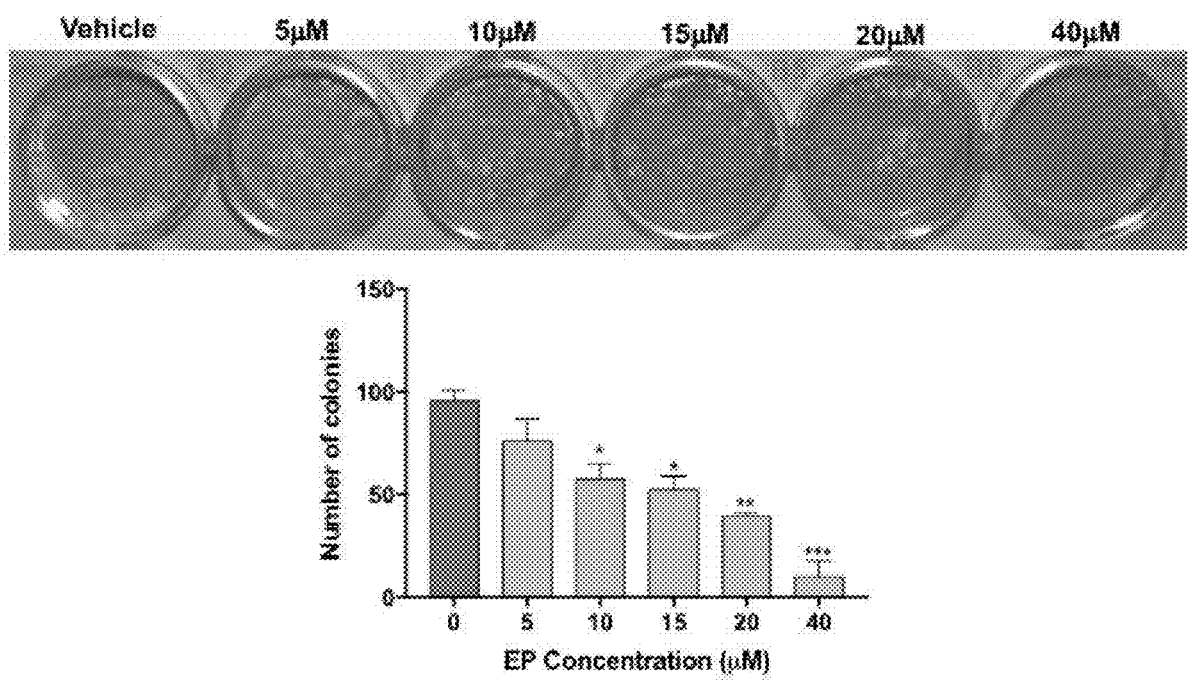
FIG. 5G. Colony formation assay in cells treated with EP for 72 h; Pictures were taken 10 d after pretreated cells were seeded at 200 cells/mL in graph; Bars represent mean±SEM. *P<0.05, P<0.01, *P<0.001, ****P<0.0001 compared to vehicle.

Cells commonly fail to bypass the G1 phase of the cycle due to mutations or DNA damage, which can result in apoptosis. Hence, to determine whether EP induces programmed cell death in SUM-149 cells, treated cells were double-stained with Annexin V and 7-AAD dyes to determine the percentage of cells in early vs. late apoptosis as well as the percentage of viable cells. As shown in FIG. 5B, the percentage of cells in early apoptosis (Annexin+, 7AAD−) significantly increased (P<0.0001) and that of live cells decreased (~15%; Annexin−, 7AAD−) after 48 h of EP treatment (P<0.0001), confirming the expectation of apoptosis induction. In addition, caspase 3/7 activity assays were performed as an alternate method of apoptosis detection. Both GA-01 and EP (FIG. 5C) increase caspase 3/7 activity and decrease viability of both SUM-149 and MDA-MB-231 TNBC cells, substantiating the death-inducing effects of GLE chemical bioactive constituents. Finally, a concentration-dependent decrease in the number and size of colonies formed upon EP treatment of SUM-149 cells (FIG. 5D), were shown further confirming the cell-cycle arrest and death-inducing effects of EP.

EP Effects on Protein Synthesis and ROS Formation

Previously a 24 h treatment of whole mushroom GLE was shown to induce ~50% protein synthesis inhibition in SUM-149 TNBC cells. To test whether GA-01 or EP derived from GLE induce de novo protein synthesis inhibition, they were tested in TNBC models following an in-cell-click de novo protein synthesis assay by treating cells for 2 h under the same conditions used for the known protein synthesis inhibitor cycloheximide Results show that EP and GA-01 do not inhibit de novo protein synthesis under these experimental conditions (FIG. 6).

Figure 7A:
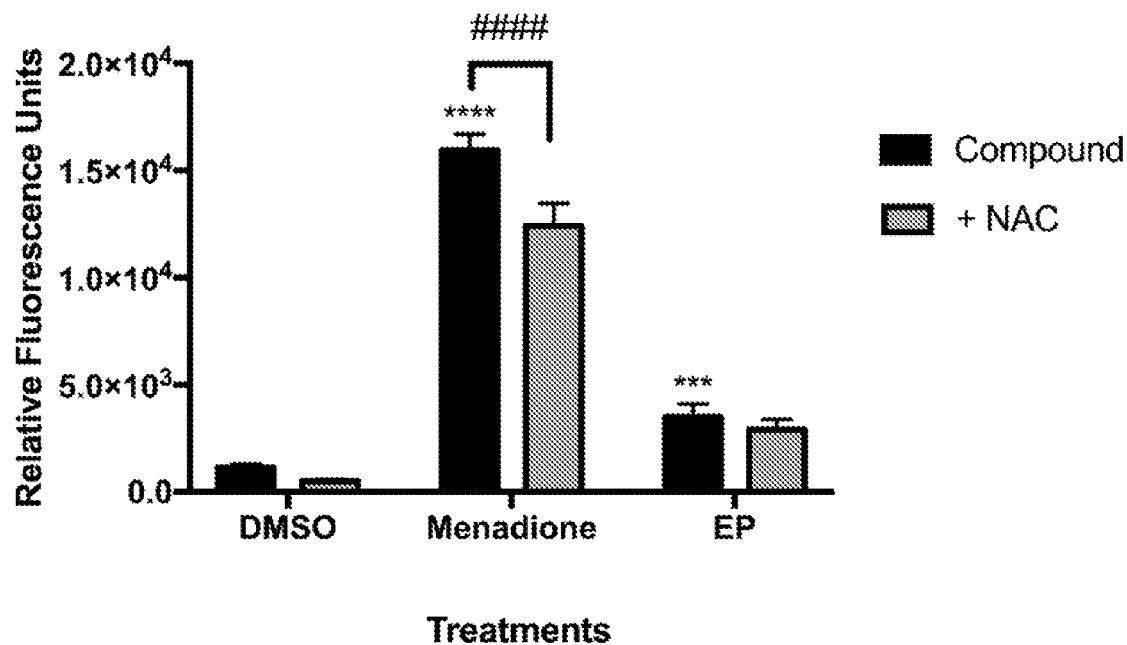
FIG. 7A.-7B. Reactive oxygen species (ROS) formation in MDA-MB-231 and SUM-149 cells.
Figure 7B:
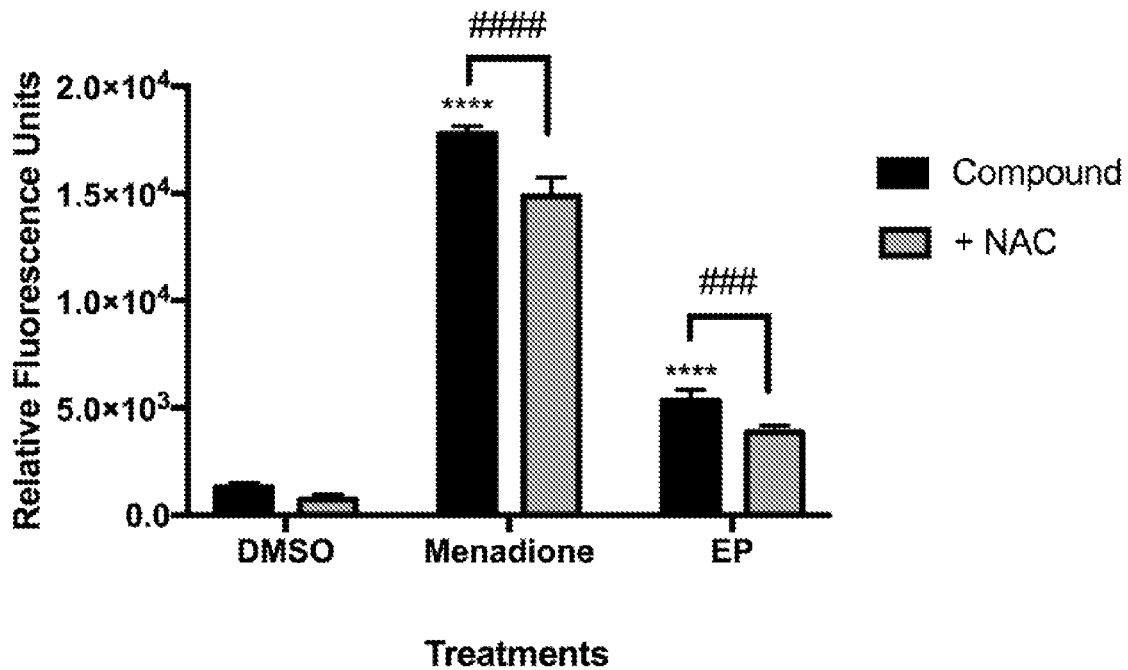

To determine whether the individual compounds affected reactive oxygen species (ROS) formation in SUM-149, MDA-MB-231 and in MCF-7 breast cancer cells. Live-cell CellROX® assays for oxidative stress detection were conducted to evaluate whether GA-01, ergosterol, 5-6-dihydroergosterol and EP trigger intrinsic apoptosis pathways by inducing ROS. CellRox® green reagent is a permeable dye with weak fluorescence while in a reduced state and exhibits bright green photostable fluorescence upon oxidation by ROS. Menadione or t-Butyl hydrogen peroxide (TBHP) were positive controls (FIGS. 7 and S5) and co-treated with N-acetyl cysteine (NAC) to confirm that the signal was due to ROS formation induced by the compound. In MDA-MB-231 and SUM-149 cells, menadione treatment caused similar effects, there was a significant reduction (P<0.0001) in ROS formation in the presence of NAC of about 20%, which might indicate increased glutathione levels, directly interacting with ROS to generate a cysteine disulfide molecule or direct interference with the compound. EP significantly induced a 2-fold ROS formation (P<0.001) for MDA-MB-231 (FIG. 7A) and a 4-fold ROS formation (P<0.0001) in SUM-149 cells (FIG. 7B). Importantly, there was a significant reduction (P<0.001) in ROS formation of about 20% in SUM-149 cells in the presence of NAC, suggesting that EP's effect is more pronounced in SUM-149 cells. In MCF-7 breast cancer cells, TBHP treatment reduced ROS formation in the presence of NAC by almost 50%. GA-01, ergosterol, 5-6-dihydroergosterol and EP induced at least a 2-fold ROS increase; but unlike TBHP, only 9-25% ROS formation reduction was observed when co-treated with NAC, and none of these results were statistically significant. Furthermore, the possibility of the endoperoxide motif to react with NAC, was assessed EP was incubated with NAC in DMSO for 24 h at 37° C. The reaction mixture was monitored by NMR and LC-MS and no observable olefin migration or opening of the endoperoxide was detected. Thus, the ability of EP to induce ROS could potentially be via a different mechanism from that of TBHP in MCF-7 cells.

Figure 8A:
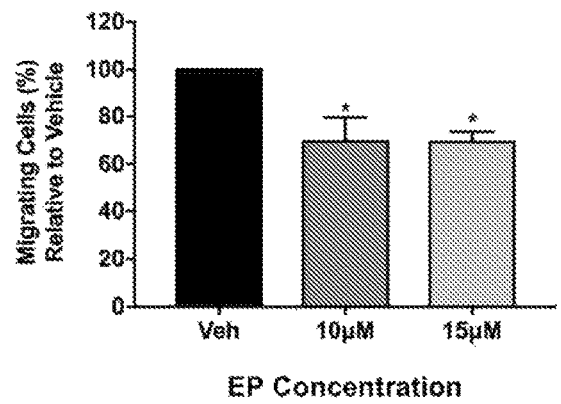
FIG. 8A.-8G. EP affects breast cancer cell migration and invasion and modulates cancer cell signaling; SUM-149 cells were treated with EP at various concentrations for 72 h as described in the Materials and Methods section.
Figure 8B:
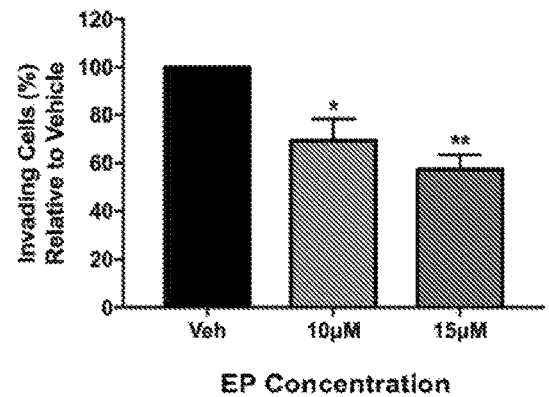
FIG. 8B. There is a concentration-dependent decrease in cancer cell invasion.

EP Reduces Cell Migration, Invasion, and Key Signaling Pathways in Breast Cancer Cells Previously, the anti-migratory activities of whole mushroom GLE in SUM-149 cells was reported. To investigate EP's effects on cell migration, Boyden chamber assays; while to investigate invasion, Transwell chambers were used. Our results show that EP decreases cancer cell migration at lower doses (10 µM) than the reported EC50 (FIG. 8A). EP shows a concentration-dependent decrease in invasion of cancer cells, as a significant reduction (P<0.05) in invading cells was observed upon 10 µM treatment. Furthermore, an additional decrease (43%) was seen when cells were treated with a non-lethal dose of 15 µM of EP (P<0.01) (FIG. 8B). These results are the first to demonstrate the anti-migratory effects of EP in SUM-149 IBC cells.

Studies that focus on drivers of cancer cell survival and invasion signaling show the important role of the AKT isoforms in breast cancer. AKT1 and AKT3 are associated with breast cancer invasion, and PTEN-deficient tumors depend on AKT2 for maintenance and survival. Disclosed results show that EP treatment significantly decreases the expression of p-AKT1 (Ser 473, P<0.01) and decreases total AKT1 (P<0.05) and AKT2 levels (P<0.001) (FIGS. 8C and 8D), while not affecting AKT3 levels in SUM-149 cells (S6). Regulation of AKT isoform expression by EP is extremely similar to what the inventors reported with whole mushroom GLE in the same breast cancer cell lines.

Figure 8C:
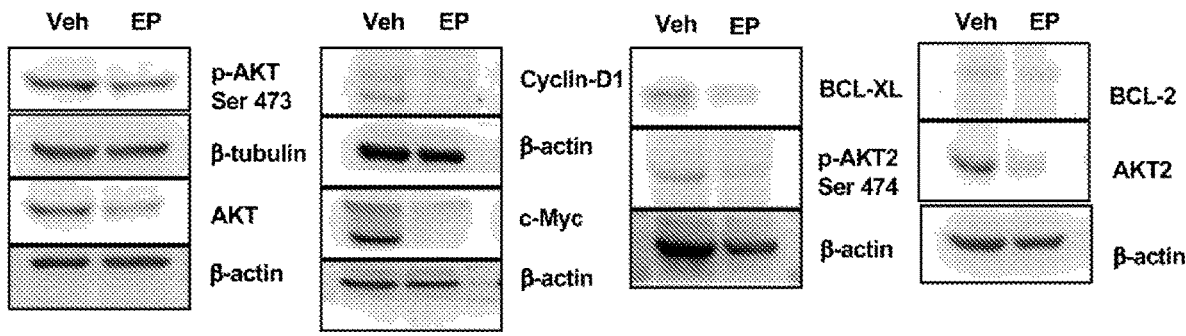
FIG. 8C. EP modulates cancer cell survival, cell death, and proliferative signaling pathways in breast cancer cells; β-actin or β-tubulin was used as a loading control.
Figure 8D:
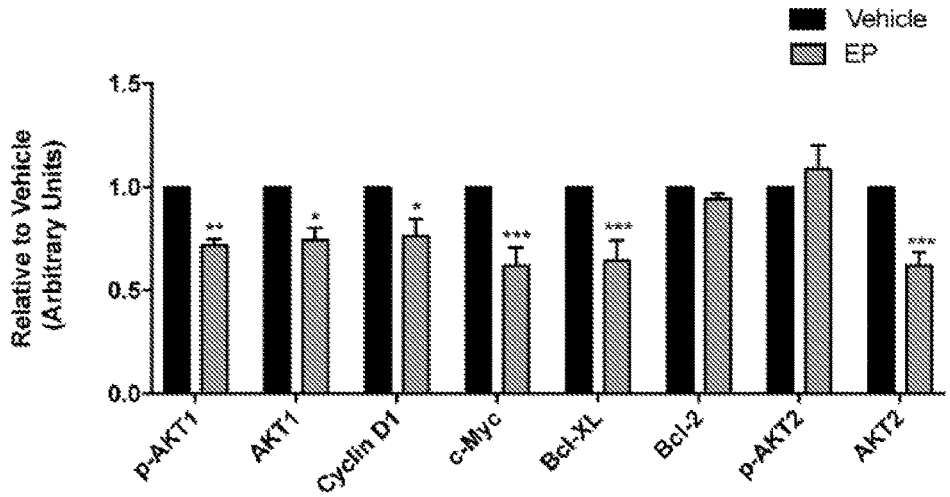
FIG. 8D. Densitometric analyses were done using Image J software.
Figure 8E:
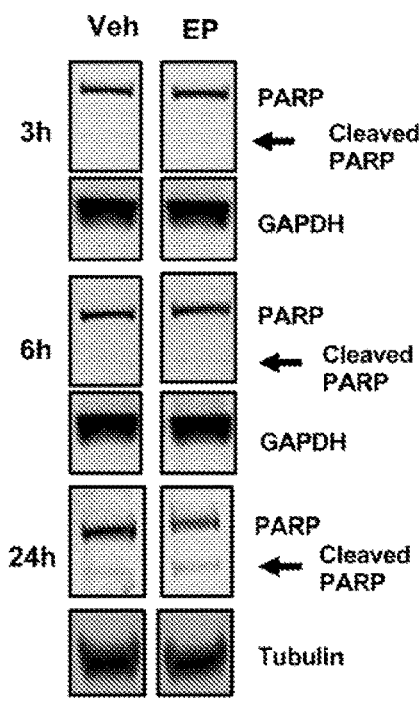
FIG. 8E. EP (30 µM) induces PARP cleavage at 24 h of EP treatment.
Figure 8F:
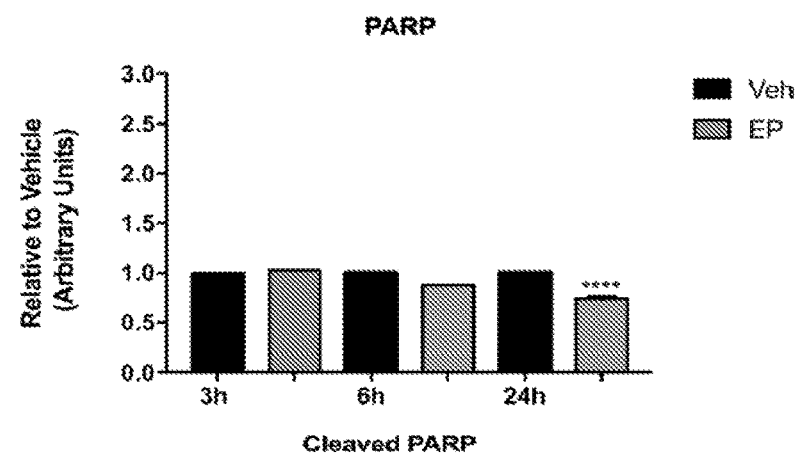
FIG. 8F. Densitometric analysis of total PARP using Image J software.
Figure 8G:
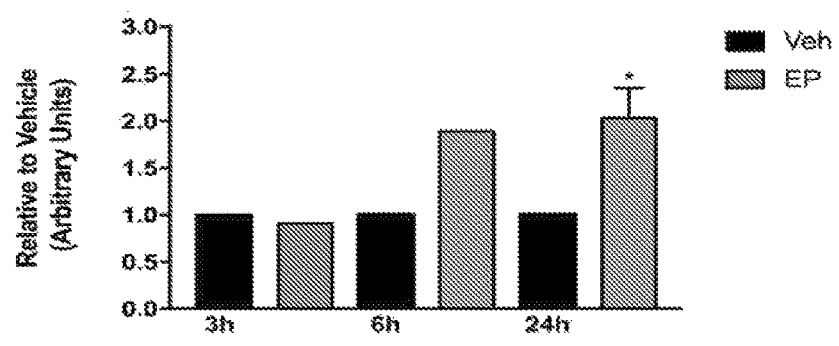
FIG. 8G. Densitometric analysis of cleaved PARP using Image J software; All Western blots presented were cropped to improve clarity; Bars represent mean±SEM of triplicates. **P<0.0001, *P<0.001, **P<0.01, *P<0.05 compared to vehicle. *P=0.03 in cleaved PARP at 24 h compared to vehicle.

Because EP induced apoptosis, its effects on the expression on anti-apoptosis proteins BCL-2 and BCL-XL, which block the release of cytochrome C from the mitochondria were investigated. As shown in FIGS. 8C and 8D, EP significantly reduces the expression of BCL-XL (P<0.001), as well as that of Cyclin D1 (P<0.05) and c-Myc (P<0.001), which are signaling molecules involved in cell cycle progression and proliferation in breast cancer cells. The apoptosis inducing effects of EP in SUM-149 cells were investigated by monitoring PARP cleavage. Results disclosed herein demonstrate EP significantly reduces total PARP levels (P<0.0001) and induces PARP cleavage (P<0.02) after 24 h of treatment in SUM-149 cells. These combined results demonstrate the inhibitory effects of EP against cancer cells, affecting migratory and death-inducing processes, as well as the expression of key proteins that play vital roles in cancer progression.

Example 2: Modifications of Compounds to Improve Efficacy

EP Derivatives

To investigate whether chemical modification would improve biological activity of ergosterol, 5-6-dihydroergosterol and EP, their corresponding neutral C-3 benzenesulfonyl carbamate derivatives were designed and synthesized. The observed modest bioactivity of these compounds was partially due to compound solubility or membrane-permeability. Therefore, introduction of a carbamate functional group as a prodrug strategy was used to improve cellular activity. The synthesis of these derivatives is shown (FIG. 9), which included the addition of benzenesulfonyl chloride (1.1 equiv.) to ergosterol (compound 4a, ergosterol sulfonamide), 5-6-dihydroergosterol (compound 5a, 5-6-dihydroergosterol sulfonamide) and EP (compound 6a, ergosterol peroxide sulfonamide) in THF at RT. The reaction was completed in good to excellent yields (87-93%). Weakly basic compounds can exist in the un-ionized or ionized form, depending on the pH of their environment and the pKa of the functional groups (—OH, —CO$_2$H). Ionized compounds may have reduced permeability across lipid bilayers relative to that of un-ionized compounds. The neutral carbamate derivatives ergosterol sulfonamide, 5-6-dihydroergosterol sulfonamide, and EP sulfonamide should have improved solubility and cross the cell membrane, resulting in a favorable, slow intracellular accumulation.

Figure 10A:
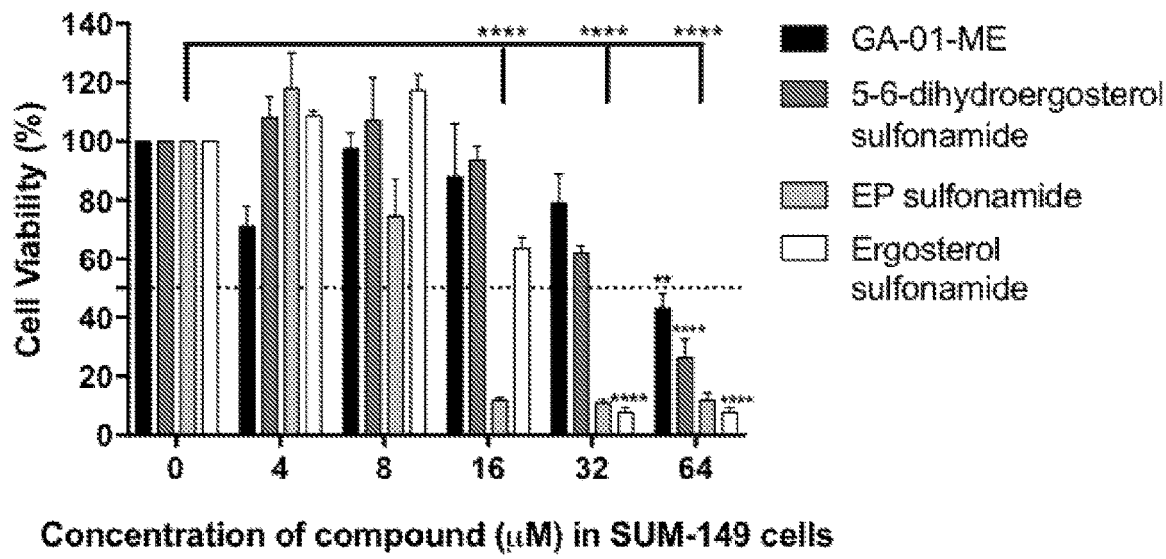
FIG. 10A.-10B. Effect of derivatives GA-01-ME, ergosterol sulfonamide, 5,6-dihydroergosterol sulfonamide and ergosterol peroxide sulfonamide in FIG. 10A. SUM-149 breast cancer cell viability and FIG. 10B. normal BJ fibroblasts viability; Cells were seeded and treated as described in the Materials and Methods section. Bars represent mean±SEM of at least 3 biological replicates. **P<0.0001, *P<0.001, **P<0.01, *P<0.05 compared to vehicle.
Figure 10B:
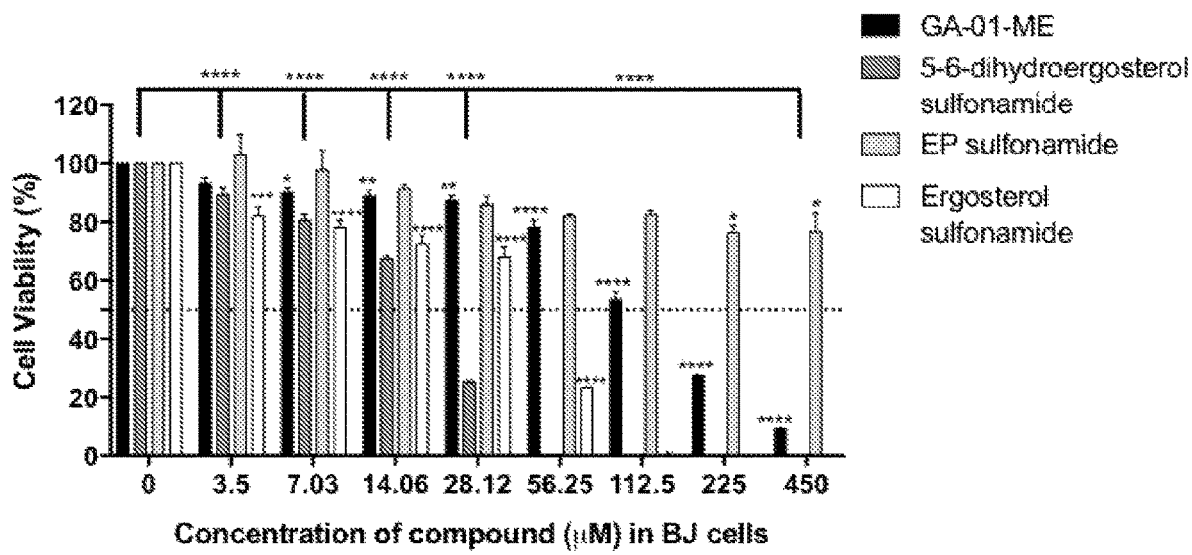
Figure 11:
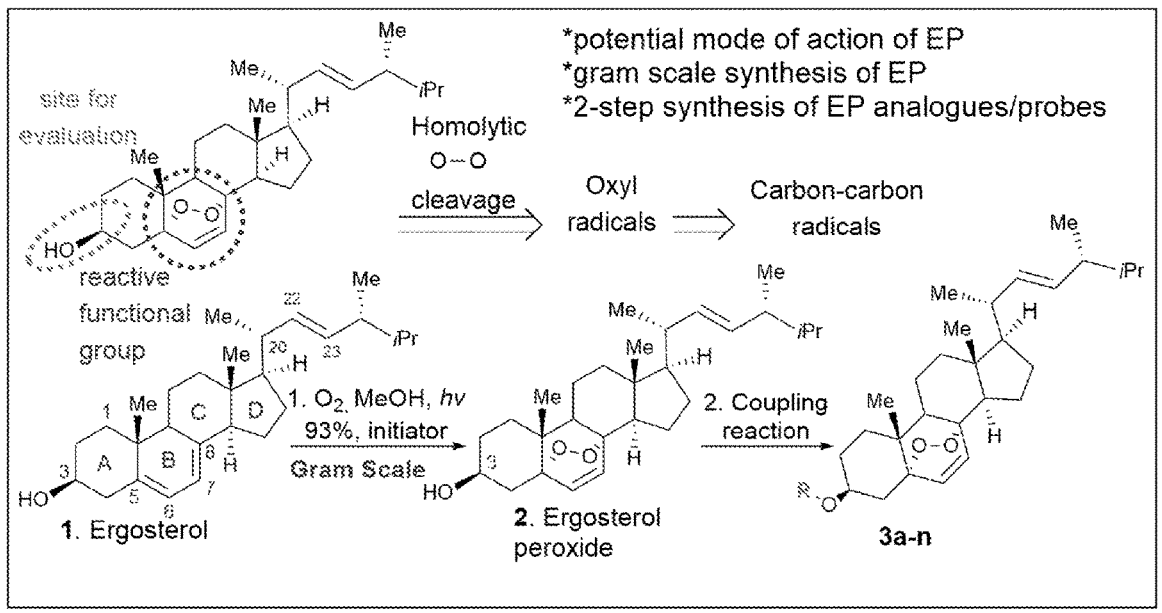

The cytotoxicity evaluation of the compounds in breast cancer cells showed improved cytotoxicity effects over those of their corresponding parental structure (FIG. 10A). EP sulfonamide shows a significant reduction in cancer cell viability (P<0.0001) with an $EC_{50}=12$ µM. Toxicity to human normal BJ fibroblasts was minimal when these cells were treated with EP sulfonamide, indicating that this compound selectively targets cancer cells (FIG. 10B). In general, the rationale behind the use of prodrugs is to optimize the physiochemical properties of the compound while maintaining the same biological profile of the parental compounds.

In the current application, the triterpene content in GLE ranged from 1-3%, but the lipid content remained consistent in 3 different batches. Triterpene content variations can occur due to differences in terpene production by mushroom or extraction methods. Herein, the seven most abundant compounds in GLE, which included ganoderic acid (GA-01), ganoderenic acid A, ganoderenic acid D, ergosterol, 5,6-dehydroergosterol, ergosterol peroxide (EP), and palmitic acid, are presented. Although previous crystal structures of ergosterol have been reported, in the present study for the first time the X-ray structure of 5-6-dihydroergosterol from *Ganoderma lucidum* was provided.

To capture potential differences in the pathobiology of cancer, the effects of the isolated compounds were tested in a representative panel of breast cancer cellular models. MDA-MB-231 and SUM-149 are triple-negative breast cancer (TNBC) cells that is, they lack the estrogen receptor (ER), progesterone receptor (PR), and human epidermal growth factor receptor 2 (HER2) and represent two distinct breast cancer subtypes: mesenchymal-like breast cancer and epithelial-like inflammatory breast cancer, respectively. SUM-190 is an IBC cell line that is ER/PR-negative but expresses the HER2 oncogene; and MCF-7 cells express ER/PR receptors (ER/PR-positive/HER2-negative). The investigation focused on testing the compounds against the most aggressive breast cancer models (TNBC and IBC) because there is a lack of therapeutic agents for successful treatment in this patient cohort.

Out of the seven isolated compounds, ergosterol displayed modest biological activity against SUM-149 cells in agreement with previous ergosterol studies in HEPG2, MCF-7 and MDA-MB-231 cell lines. EP displayed the greatest selective anti-cancer activity in the cell lines tested. EP features a cyclic peroxide (—O—O—), and these compounds are collectively known as endoperoxides. A classic example of this class of compounds is featured in the antimalarial drug, artemisinin, which has aid in reducing the widespread of drug-resistant parasites and has demonstrated cytotoxic activity. EP has been shown to have anti-cancer cell growth properties via regulation of various signaling pathways (e.g. AKT and c-myc) in a hepatocellular carcinoma cell model. Similarly, present results show that EP selectively affects cancer cell viability in various cancer models, where SUM-149 IBC cells display the highest sensitivity. Interestingly, EP treatment in normal BJ and non-cancerous mammary epithelial MCF10A cells did not show significant cytotoxicity. Studies reported herein revealed that EP induces G1 arrest in the cell cycle, which is accompanied with a decrease in cyclin D1 and c-myc expression and an increase in early apoptosis of SUM-149 cells. Comparable regulatory results were obtained in colorectal and hepatocellular cancer cell models upon EP treatment, with most cells stalled in the early stages of the cycle. Moreover, EP reduces the expression of pro-survival p-AKT1, as well as levels of total AKT1 and AKT2 without affecting p-AKT2. It is possible that EP decreases total AKT2 without affecting p-AKT2 via a feedback mechanism, which induces signals to overcome the inhibitory effects obtained on total protein. Although p-AKT2 is not significantly upregulated, the phosphorylated levels might be stabilized to compensate for loss of total AKT2. Further studies are underway to understand the cell signaling regulatory effects of EP.

EP treatment of SUM-149 cells reduced cell viability and induced apoptosis detected by an increase in caspase-3/7 activity and PARP cleavage after 24 h of treatment. EP's cytotoxicity profile in SUM-149 (TNBC/IBC) cells is consistent with that of cells exposed to a compound that induces cell-cycle arrest and early-phase apoptosis. In contrast, EP decreased cancer cell viability, while induced apoptosis via caspase 3/7 activation, and increased cytotoxicity of MDA-MB-231 TNBC cells. The combined results suggest the death-inducing effects of EP on the two TNBC cell lines occurs by different mechanisms. All the tested compounds induce ROS in breast cancer cells albeit at different levels. Specifically, EP increases ROS formation with greater capacity in SUM-149 cells, and the effects where reduced when co-treated with NAC. Therefore, intracellular ROS might be an additional contributing factor for the observed apoptotic effects of EP. Importantly, the results are consistent with the apoptosis-inducing effects of EP that have been previously obtained from distinct sources and demonstrated in various in vitro cancer models, including colorectal, prostate, and leukemia cells.

Additional cancer cell properties that increase their pathogenicity include their ability to migrate and invade to distant organ sites. Thus, the regulatory effects of non-lethal doses of EP on SUM-149 cell motility and invasion were investigated. EP displayed a reduction in cell migration and invasion, and these results are consistent with previous studies with GLE wherein reduced invasion potential of breast cancer cells was demonstrated. Moreover, present results are the first to demonstrate the anti-migratory effects of EP in SUM-149 breast cancer cells, and demonstrate anti-invasion effects at lower dosages than those reported in the literature in breast cancer lines.

One of the liabilities with EP is sharing its core with cholesterol, an amphipathic molecule with part-water soluble, part-water insoluble character. Thus, while able to readily cross the cell membrane, the ability to deliver the pure compound faces challenges. EP's solubility properties are poor in DMSO or water unless warmed up to 30° C. However, in this report, EP's derivative, EP sulfonamide, was soluble at 10 mM in DMSO. Thus, the generation of a selective anti-cancer compound with greater potency than EP, and ample therapeutic window when compared to BJ normal cells, was accomplished.

Example 3: Construction of Probes

Figure 12:
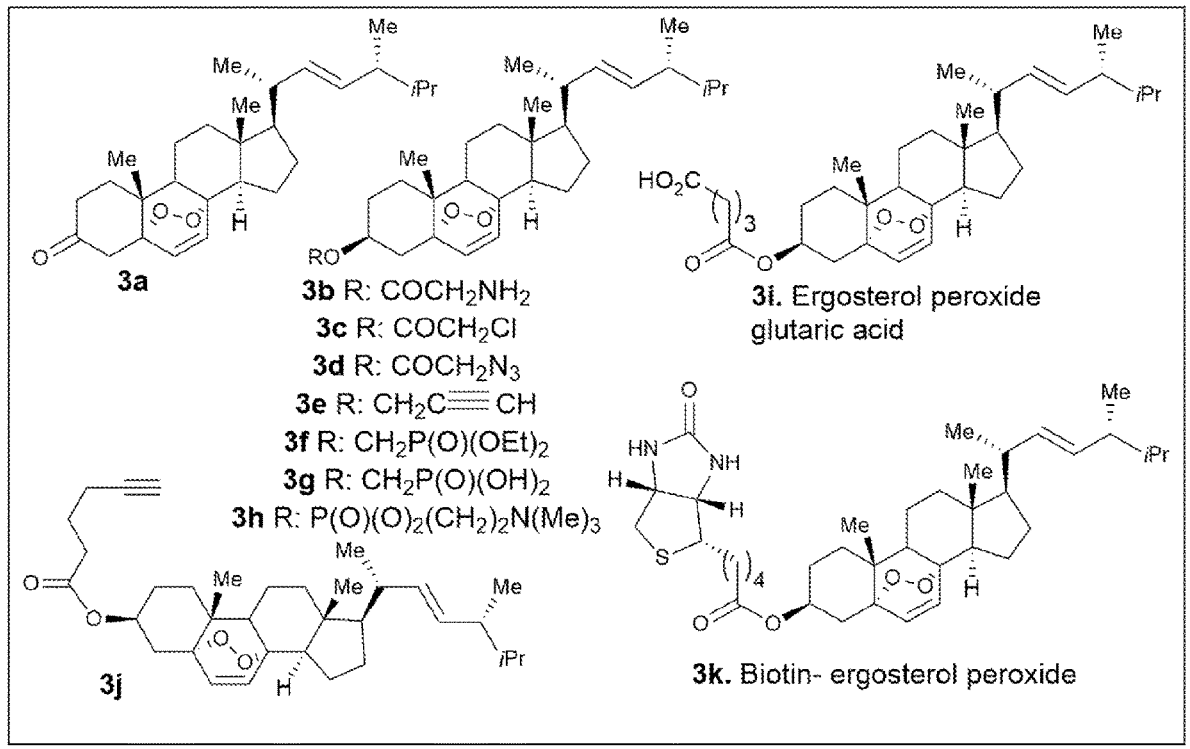

First, EP was generated from ergosterol as the starting material by treating with oxygen in the presence of radical initiator (catalytic) in MeOH via hetero Diels-Alder reaction in excellent yields (93% yield, see SI) as a single compound after purification. The free hydroxyl group at C3 offers a handle for further functionalization. Thus, several EP-analogues (3a-3k) (FIG. 12.) were generated to evaluate the influence of the length and nature (polar groups) of the linker to the C3-hydroxyl group in terms of cytotoxicity. Previously, benzyl carbamates of EP were observed to display improved biological activity presumably due to improved solubility properties.

Figure 15:
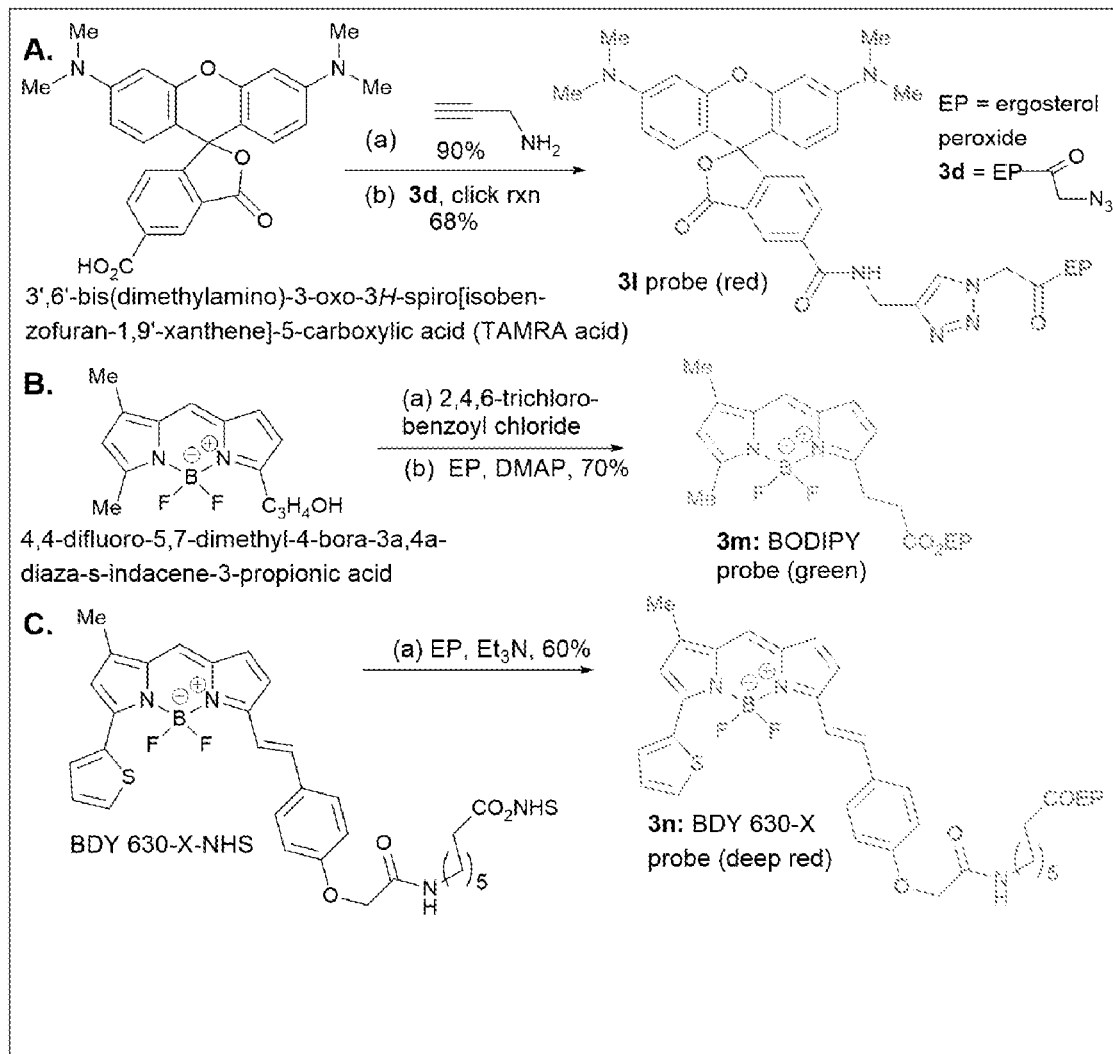

Oxidation of compound 3 with TPAP/NMO at RT provided the enone system 3a. In parallel, synthesis of 3b-3c, 3h, 3i, 3j and 3k involved esterification of EP with the corresponding carboxylic acid, acyl chloride, or anhydride (See SI for detailed information). Synthesis of 3d-3g involved $S_N2$ type of reactions. Synthesis of the biotinylated compound involved the coupling of EP with the mixed anhydride of biotin in good yield. The synthesized compounds were characterized by $^1H$ and $^{13}C$ (1D and 2D) NMR and mass spectrometry. Next, the generation of the EP fluorescent probes (3l-3n) was generated for live cell analysis including organelle detection and studies on function (FIG. 15.). Conjugation of EP with fluorescent dyes such as TAMRA (tetramethylrhodamine), FITC (fluorescein isothiocyanate derivative), and BODIPY (boron-dipyrromethne derivative) was contemplated. These fluorescent probes must be orthogonal to other organelle-fluorescent trackers during the co-localization studies using fluorescent microscopy. Bu et al. generated a coumarin fluorescent probe of EP, which is known to accumulate to the mitochondria. The unbiased fluorescent EP probes disclosed herein were intended to undercover the specific site of accumulation of EP without influence of the fluorescent tag and provide insight into the mechanism of EP. The fluorescent reagents can affect the motility of the parental compound, as well as the site of accumulation, minimizing the size of the linker was minimized to maintain the molecular weight range compared to the parental EP. The rhodamine probe (tetramethylrhodamine, TAMRA), structure is shown in FIG. 15.

Treatment of commercially available 5-TAMRA (5-carboxytetramethylrhodamine), propargyl amine (2 equiv.) with PypOP and Hünig's base afforded the corresponding FITC-propargyl amide (90% yield). Next, the synthesis of EP-azide was achieved via: (a) acylation of EP with acyl chloride, followed by (b) azide displacement under basic conditions. The copper-catalyzed azide-alkyne cycloaddition (CuAAC) was mediated by catalytic copper sulphate in the presence sodium ascorbate in t-BuOH and water to provide 3l in 68%. The BODIPY derived probes were generated by treatment of BODIPY propianate with activating 2,4,6-trichlorobenzoyl chloride in the presence of $Et_3N$, and subsequently addition of EP resulting in compound 3m. A single-step condensation of the corresponding N-hydroxysuccinimide ester of a BODIPY deep red fluorescent reagent, affording 3n in 60% yield.

To better understand the structure-activity-relationship of EP, its core was modified at the C3 position of the steroid backbone. From the evaluation of ergosterol, it had become clear to us that the endoperoxide is a required functional group for potent activity against cancer cell models. To assess the cytotoxicity of these compounds, CTG (CellTiterGlo assay) was used for 72 hr as shown in Table 1. The triple negative breast cancer cell lines: MDA-MB-231, SUM-149, and the ER positive cell T47D. Both normal cell lines HMEC and BJ cells were also evaluated to determine therapeutic index. Results showed that the TNBC model SUM-149 was the most sensitive cell line towards all the compounds, while MDA-MB-231 was less responsive. The ER positive cell line T47D was the least responsive under the studied conditions. EP (compound 3) has been reported to have variable potency across cancer cell lines, which can be directly attributed to its poor solubility. While 3 is surprisingly stable, and only one report disclosed the conversion of 3 to ergosterol presumably via retro-Diels-Alder react. No degradation by MS/MS in PBS over 72 hr at 37° C. was observed. However, precipitation of compound 3 is formed over 168 hr at RT, affecting molarity. Furthermore, some of the generated compounds also displayed poor solubility properties, indicating that liposomal delivery will be a suitable future strategy to overcome this potential liability.

Noteworthy, the oxidized compound 3a displayed improved activity, which was partially attributed to improved solubility properties. The corresponding amine (3b), chloride (3c), azide (3d) showed promising activity against SUM-149 with little or no activity observed at the tested concentrations in MDA-MB-231 and T47D. The corresponding alkynyl ether 3e showed better activity, while the compound 3j containing the longer chain showed superior activity across cell lines. The phosphonate ester 3f showed improved activity while the corresponding phosphonic acid (3g), the phosphocholine (3h) and glutaric ester (3i) displayed poor activity, presumably due to the charged nature of these compounds. The biotinylated compound 3k showed comparable cytotoxicity to the parental compound 3. The TAMRA-probe 3l showed poor solubility properties and precipitated readily in DMSO or PBS. Washout experiments revealed that the compound 3l did not accumulate in the cell at all. It is possible that the observed cytotoxicity arises from interfering with nutrient intake, but not via apoptosis due to the short, if any residency time inside the cell. Lastly, the fluorescent probes 3m demonstrated comparable cytotoxicity to the parental compound 3. However, 3n showed superior activity. It is also important to highlight that compound 3 and its chemical analogues displayed moderate therapeutic index at the tested concentrations, especially promising for compound 3k, 3m-3n, which is comparable to the FDA approved drug (capecitabin). The ability to induce apoptosis and not only anti-proliferative effects of these compounds was validated via propidium iodide assay for the 3k, 3m-3n.

Next, to evaluate the subcellular co-localization of EP, engineered orthogonal cellular models were generated. The synthetic chemical probes are more cost effective over genetic cellular manipulations and can be available in higher quantities. They can also have a wide range of built-in reporting and targeting features, making them versatile research tools. Their use in cells does not require transformation or manipulation of the cell. Although chemical probes were used with commercially available dyes, no orthogonal dye was available for our chemical probes to study golgi and peroxisome. Therefore, for the transiently transfected cellular models, BacMam technology was applied for MDA-MB-231 and SUM-149 (as shown in FIG. 3A.-3B.).

Figure 13:
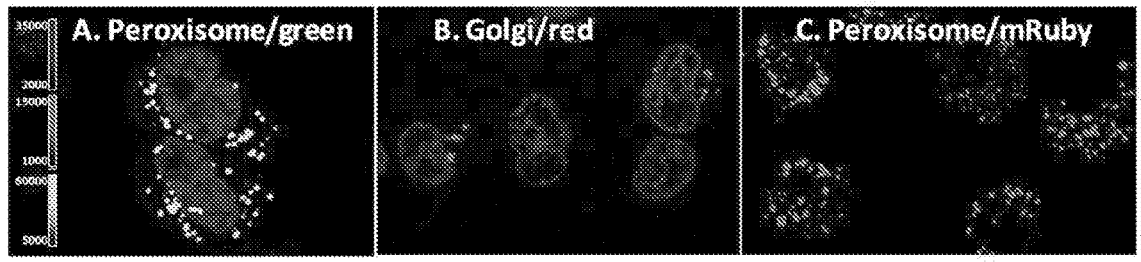

For the Ruby-peroxisome tagged organelle, stable MDA-MB-231 cells were generated (FIG. 13.).

Figure 14A:
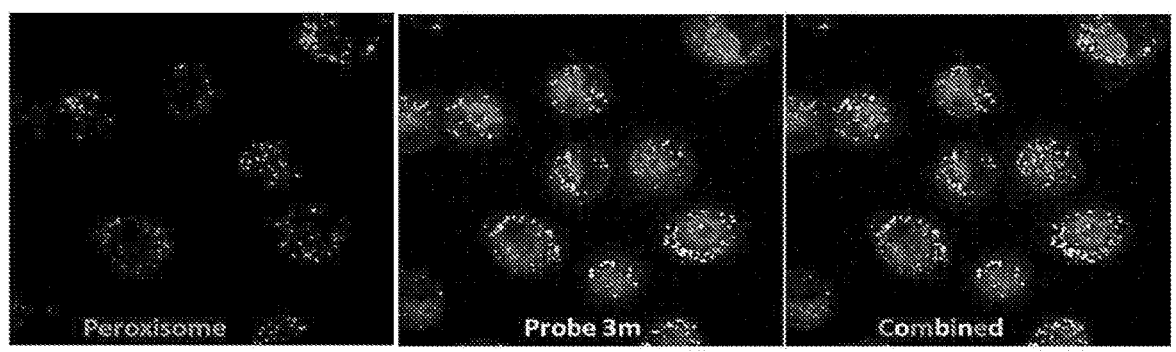
FIG. 14A.-14E. Co-localization studies of 3m in MDA-MB-231.
Figure 14B:
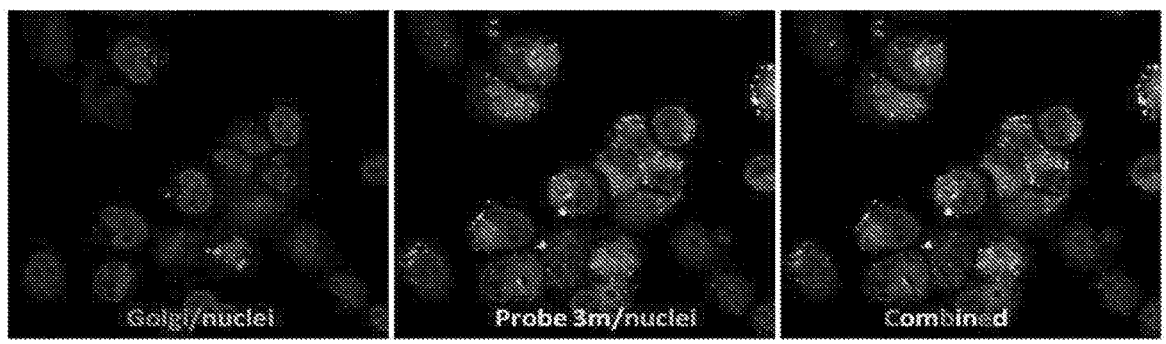
FIG. 14B. Golgi.
Figure 14C:
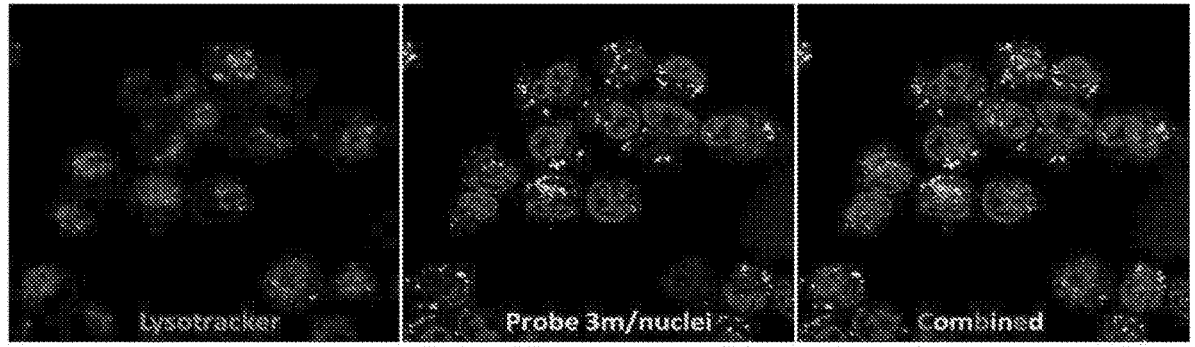
FIG. 14C. Lysosome.
Figure 14D:
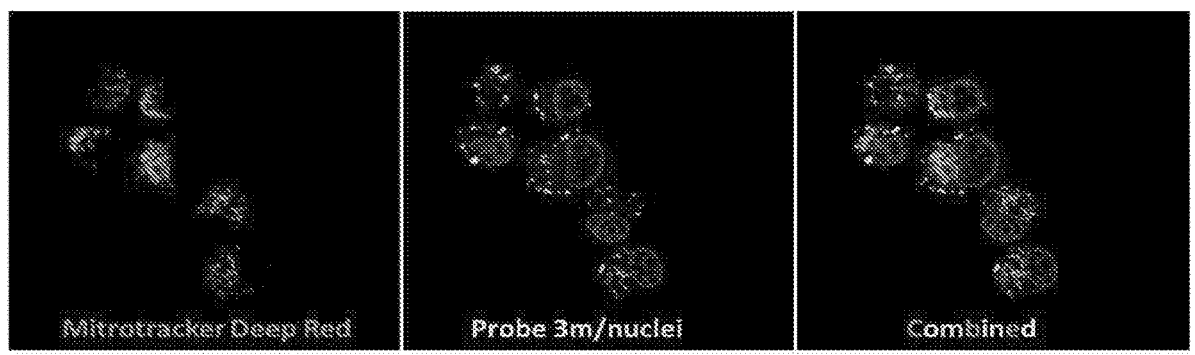
FIG. 14D. Mitochondria.
Figure 14E:
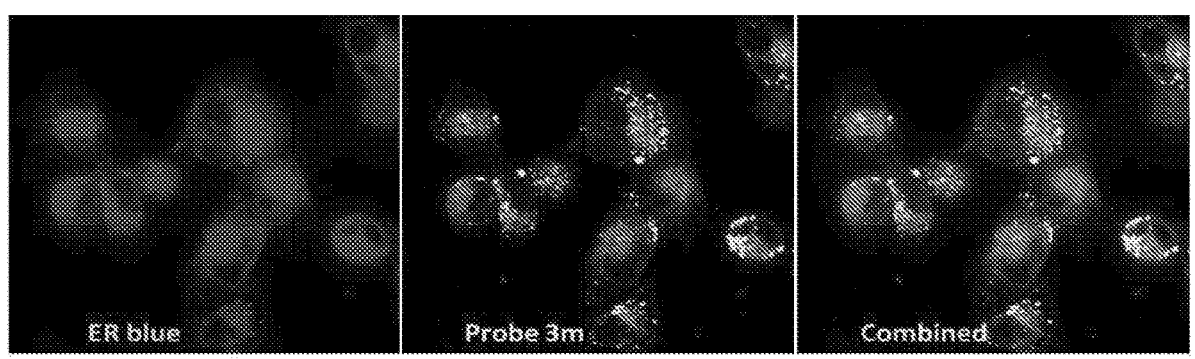
FIG. 14E. Endoplasmic reticulum.

EP is an endoperoxide, EP would likely accumulate in the peroxisome. Probe 3l was first evaluated and as previously mentioned, no cell staining was observed as the compound had difficulties penetrating the cell. As shown in the washout experiments of probe 3m, indicated that the compound distributes across the cytosol. Then, compound 3m was evaluated in the Ruby-red peroxisome stably transfect cells (FIG. 14A.), no co-localization was observed. The same observation was determined for golgi-RFP cells (FIG. 14B.). To access whether 3m accumulated in the lysosome, lysotracker was used (FIG. 14C.), and no co-localization was recorded. Next deep red mitotracker was used to evaluate mitochondrial co-localization, and no overlap was detected (FIG. 14D.). Finally, by using blue/white ER tracker along with 3m, good co-localization was recorded (FIG. 14E.). Consistent observations were recorded in both MDA-MB-231 and SUM-149 cancer cells. Because this chemical probe had similar efficacy in the cell as EP, the combined results suggest that it is likely that EP resides in the cytosol of the cell, and partially co-localizing in the ER.

Also, the deep-red EP probe (3n) was generated and evaluated to determine whether a similar localization pattern would be observed. In the GFP-peroxisome cell lines, a different pattern was observed from 3m as shown in FIG. 5A. As the accumulation appeared quite different, green mitotracker was used to investigate the compound distribution in the cell. Unexpectedly, 3n selectively accumulated in the mitochondria. Such finding was congruent with our finding that this compound was the most potent of all evaluated derivatives across cell lines, as it can induce more cellular damage if it resides in the mitochondria.

The target deconvolution to study the mode of action of NPs and drugs remains one of the biggest challenges in chemical biology today. However, affinity-based proteomics are still the most common and leading methods to accelerate biological target identification in drug discovery. Thus, a pulldown experiment was designed with the biotinylated probe 3k, which showed similar efficacy to EP. Incubation of the biotinylated probe bound to beads with cells lysates avoids some of the issues related with compound solubility, and the secondary effects during cell death. As the control, the non-cytotoxic biotinylated cholesterol probe proved an excellent probe and added a significant advantage of targeting all the non-selective proteins. The outcome provides insight into potential protein interactors. The distribution of potential biological targets interacting with 3k in SUM-149 and MDA-MB-231 cell models are shown in FIG. 18. The spectral counting performed well displaying significant p-values of the potential targets. Two targets (RIPL2 and UBR4) were identified in both SUM-149 and MDA-MB-231 cell lines, which are both distributed across the cytosol and the plasma membrane which would agree with our co-localization studies. Rab Interacting Lysosomal Protein Like 1 (RLP1 also known as RILPL1), plays a role in the regulation of cell shape and polarity due to its role in cellular protein transport. E3 ubiquitin-protein ligase (UBR4) interacts with the retinoblastoma-associated protein in the nucleus and with calcium-bound calmodulin in the cytoplasm. UBR4 is also a component of the N-end rule pathway, which recognizes and binds to proteins bearing specific N-terminal residues that are destabilizing according to the N-end rule, leading to their ubiquitination and subsequent degradation. This protein coupled with clathrin, forms meshwork structures involved in membrane morphogenesis and cytoskeletal organization and regulates integrin-mediated signaling. Further validation studies are warranted to elucidate the exact mode of action of this natural product. EP has potential as a hit compound for further therapeutic development, and chemical modifications can lead to superior potency by accumulating in specific organelles to induce greater cellular effect.

Example 4: In Vivo Study of Efficacy of Ergosterol Peroxide in Producing Tumor

Progression
1. Experimental Design

Female severe combined immunodeficient (SCID) mice (21 d of age) were purchased from Charles River Laboratories International Inc. (Wilmington, MA) and housed under specific pathogen free conditions. The mice received autoclaved AIN 76-A phytoestrogen-free diet (Tek Global, Harlan Teklad, Madison, WI) and water ad libitum. This protocol was approved by the Universidad Central del Caribe IACUC. Cell inoculations were performed as previously described by the inventors (PMID: 20517637, PMID: 23468988, PMID: 26958085, PMID: 30542507, PMID: 31658643). MDA-MB-231 GFP cells ($5\times10^5$) in Matrigel (BD Biosciences, San Jose, CA) were injected into the mammary fat pad. After tumor establishment the animals were randomly divided into control and experimental groups. Treatment started on week 5 post-inoculations when tumors were ~100 $mm^3$. SCID mice (n=8/group) were injected i.p. with vehicle (10% ETOH in 1×PBS), 100 mg/kg BW ergosterol peroxide in a 100 uL volume three times per week.

2. Intravital Imaging

The mice were imaged following tumor establishment, and once per week thereafter. Tumor progression was monitored by fluorescence image analysis taken on an UVP iBox Explorer (Analytik Jena, Upland, CA) and quantified as in PMID: 20517637. Relative tumor growth was calculated as the fluorescence intensity of each tumor on day of imaging. Quantification for tumor progression was calculated using the fluorescence intensity of each treated tumor relative to the fluorescence intensity of the same tumor on d 01 of treatment administration (week 5) using ImageJ software (National Institutes of Health, Bethesda, MD).

3. Statistical Analysis

To account for the time horizon as a statistical unit, a General Linear Model Repeated Measures ANOVA approach was used. Bonferroni post-hoc test was used for multiple comparisons, and the significant level ($\alpha$) was set to <0.05.

Figure 16A:
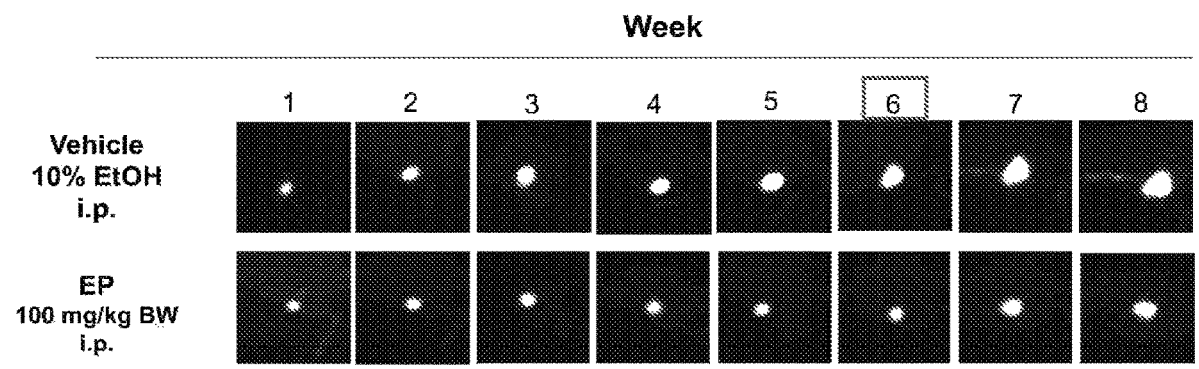
FIG. 16A.-16B. MDA-MB-231-GFP cells (5.0×105) were injected in the lower right mammary fat pad of female hairless severe combined immunocompromised mice.
Figure 16B:
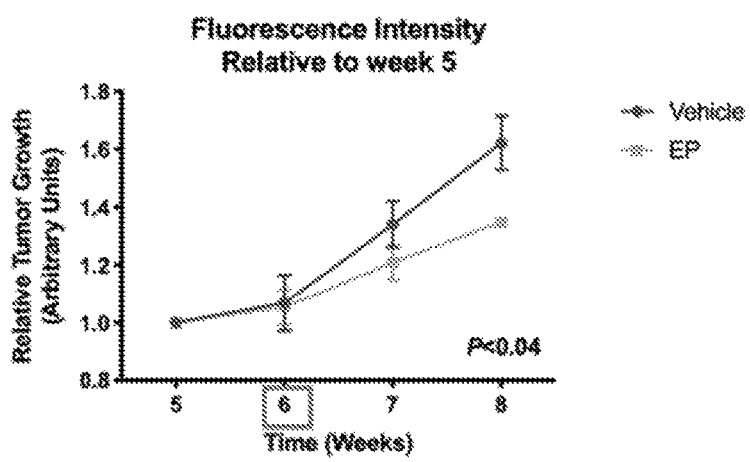
FIG. 16B. Mammary tumor growth was quantified as changes in the integrated density of GFP fluorescence, relative to week 5. Results show that EP significantly decreases (P<0.04) tumor growth rate. Mean±SEM of three representative mice per treatment.
Figures 19A, 19B:
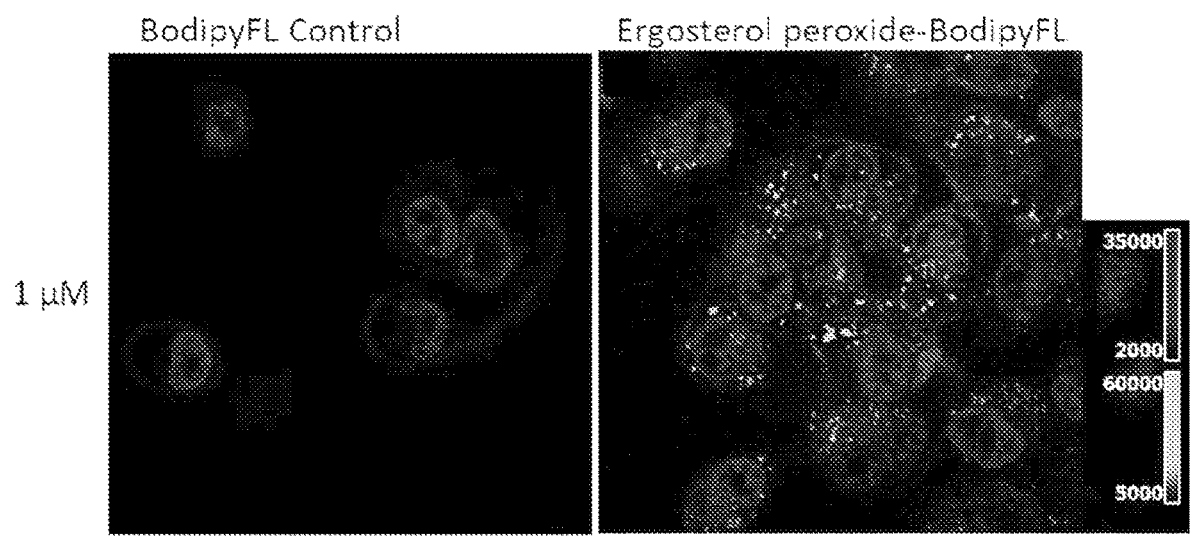
FIG. 19A.-19B. representative images of washout experiment of BodipFl methyl ester control and ergosterol peroxide-BodipyFl probe 3m both at 1 µM using MDA-MB-231 cellular model and nuclear stain Hoechst 33342.
FIG. 19B. Fluorescence of compound 3m is observed after washing, indicating intracellular accumulation.
Figures 20A, 20B, 20C:
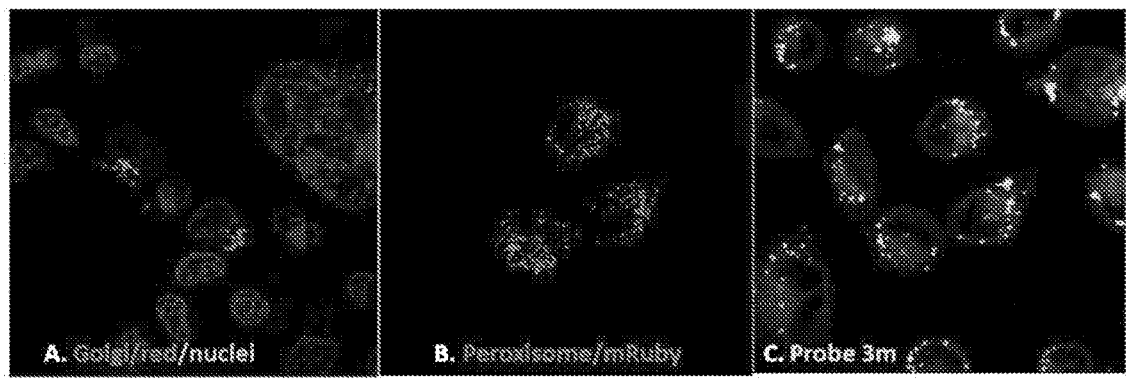
FIG. 20A.-20F. are representative images of co-localisation studies in SUM-149 cells with probe 3m (EP-BodipyFl)
FIG. 20B. stably mRuby-peroxisomes-2 SUM-149.
FIG. 20C. BodipyFl.
Figure 20D:
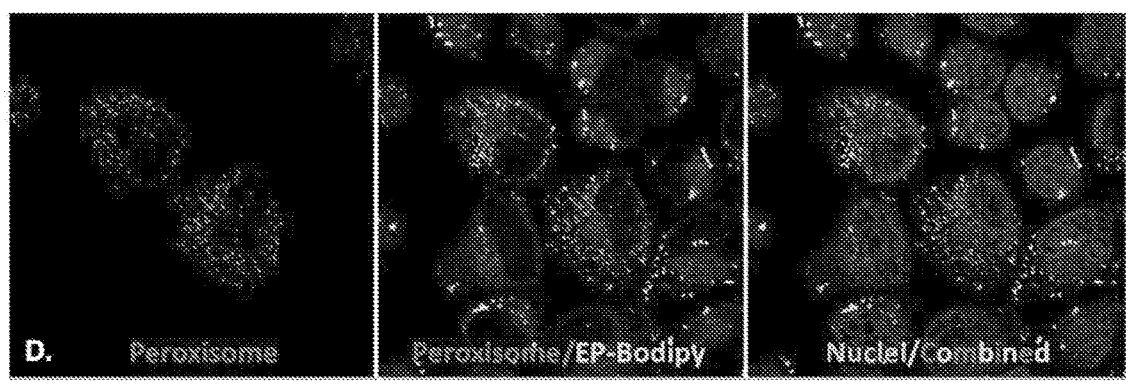
FIG. 20D. Peroxisome stable transfected cells, colocalisation with 3m.
Figure 20E:
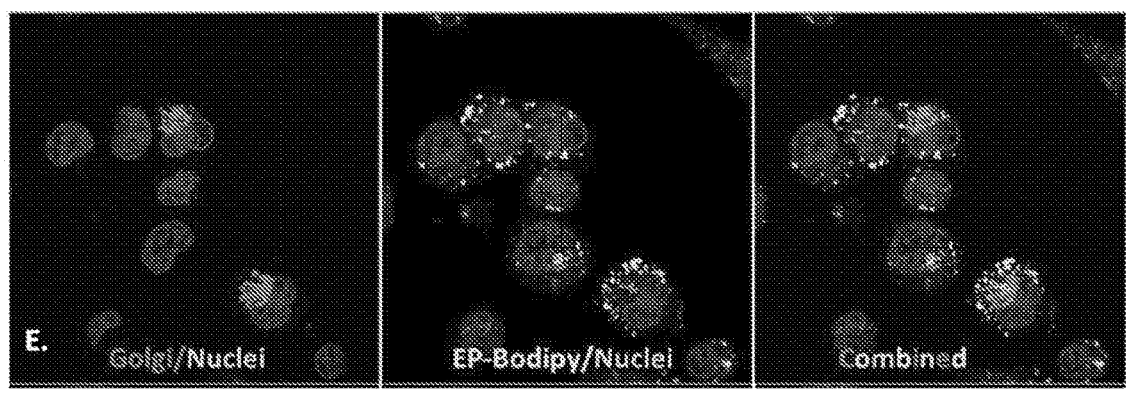
FIG. 20E. RFP-Golgi transfected cells co-localisation with 3m.
Figure 20F:
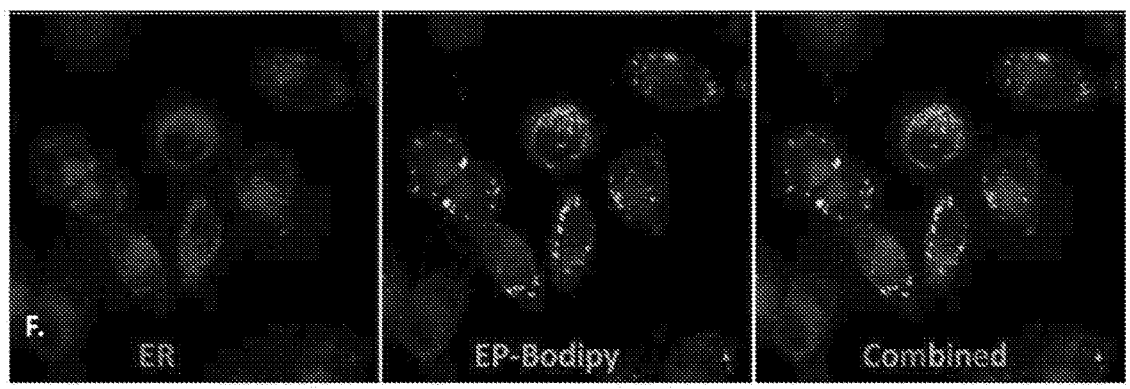
FIG. 20F. endoplasmic reticulum Tracker, co-localisation with 3m.

For results see FIG. 16(A, B).

Materials and Methods

A. Experimental Chemistry Procedures
1. General Information:

Capsules (500 mg) of commercially available whole mushroom ReishiMax GLp™ (Pharmanex Inc., Provo, UT), consisting of powdered *Ganoderma lucidum* extract (GLE) fruiting body and cracked spores were used [12-14]. All manipulations were carried out under inert gas atmosphere unless otherwise noted. Anhydrous tetrahydrofuran (THF), diethyl ether ($Et_2O$), dichloromethane ($CH_2Cl_2$), toluene ($PhCH_3$), acetonitrile ($CH_3CN$), methanol (MEOH), and dimethylformamide (DMF) were obtained from a solvent drying system. Reagents of the highest available quality were purchased commercially and used without further purification unless otherwise stated. Title compounds were purified by flash column chromatography using E. Merck silica gel (60, particle size 0.040-0.063 mmol) or Biotage Isolera Four with normal-phase silica gel. Reactions were monitored by thin-layer chromatography (TLC) on 0.25 mmol E. Merck silica gel plates (60E-254), using UV light for visualization and an ethanolic solution of anisaldehyde, or PMA, CAM solutions and heat as developing agents.

Reactions were also monitored by using Agilent 1100 series LCMS and low-resonance electrospray ionization (ESI) model with UV detection at 254 nm. The structures of the synthesized compounds were confirmed by $^1$H and $^{13}$C-NMR that were recorded on 400/or 500 MHz Bruker AVANCE III HD NMR. Chemical shifts were reported as ppm relative to the solvent residual peak (CHCl$_3$: 7.26 ppm for $^1$H, 77.2 ppm for $^{13}$C; acetone-d$_6$: 2.05 ppm for $^1$H, 29.9 ppm for $^{13}$C; Pyridine d$_5$: 2.50 ppm for $^1$H, 39.5 ppm for $^{13}$C). Data are reported as follows: chemical shifts, multiplicity (s=singlet, d=doublet, t=triplet, q=quartet, quint=quintet, m=multiplet, br=broad), coupling constant (Hz), and integration. Data were processed by using MestReNova. Optical rotations were measured on a DCIF polarimeter (JASCO P-1010) using a 2-mL cell with a 100-mm path length. High-resolution mass spectra (HRMS) were recorded on an Agilent ESI-TOF (time of flight) mass spectrometer using matrix-assisted laser desorption ionization (MALDI) or electrospray ionization (ESI) or on a Waters Xevo G2 Q-ToF mass spectrometer. Compounds were analyzed by using ESI in positive-ion mode. The purity of each synthesized compound was determined on a Waters ACQUITY UPLC-PDA-ELSD-MS system using a C18 reverse phase column and 0.1% formic acid/water-0.1% formic acid/acetonitrile as the solvents. All synthesized compounds were at least 95% pure based on analytical HPLC and NMR. Chemical yields refer to purified compounds ($^1$H-NMR).

2. Bioactivity Fractionation of GLE (Fraction 1-100):

As previously described by Tu [15], preparative HPLC separations were performed on a Gemini 5-μm C18 110A column (30×50 mm, 5 μm, Phenomenex, Inc., Torrance, CA). A Shimadzu LC-8A binary preparative pump with a Shimadzu SCL-10A VP system controller was connected to the Gilson 215 auto sampler and Gilson 215 fraction collector (Gilson, Inc., Middleton, WI). Detections were performed by a Shimadzu SPD-M20A diode-array detector and a Shimadzu ELSD-LT II evaporative light-scattering detector (Shimadzu Corp., Kyoto, Japan). The mobile phase consisted of water (A) and Acetonitrile (B): 0 min, 98:2; 0.5 min, 98:2; 6.5 min, 0:100; 12.3 min, 0:100; 12.5 min, 98:2; 12.95 min, stop. The flow rate was 25 mL/min. Briefly, fractions (A—fractions 1-6, B—fractions 7-9, C—fractions 10-17, D—fractions 18-31, E—fractions 32-41, F—fractions 42-100) were collected and combined based on mass spectra data; their TLC profiles and biological properties were evaluated.

3. Crystal Structure of Ergosterol (Compounds 4) and 5,6-dehydroergosterol (Compound 5):

Fraction 98 and 99 (out of 103 fractions collected) precipitated and crystals were collected for single crystal diffraction studies conducted on a Bruker Kappa APEX-II CCD diffractometer equipped with Cu K$_\alpha$ radiation ($\lambda$=1.5478). Crystals of the subject compound were grown by dissolving approximately 1 mg of sample in 350 μL of Ethyl Acetate, which was then vapor diffused with Pentane over several days. A 0.114×0.085×0.076-mm piece of a colorless block was mounted on a Cryoloop with Paratone oil. Data were collected in a nitrogen gas stream at 100(2) K using φ and $\overline{\omega}$ scans. Crystal-to-detector distance was 40 mm using variable exposure times (10 s-60 s) depending on θ, with a scan width of 1.0°. Data collection was 96.2% complete to 67.614° in θ (0.83 Å). A total of 37758 reflections were collected covering the indices, $-12<=h<=12$, $-8<=k<=8$, $-40<=l<=40$. A total of 8970 reflections were found to be symmetry independent, with an R$_{int}$ of 0.0582. Indexing and unit cell refinement indicated a primitive, monoclinic lattice. The space group was found to be P2$_1$. The data were integrated by using the Bruker SAINT software program and scaled by using the SADABS software program. Solution by direct methods (SHELXT) produced a complete phasing model consistent with the proposed structure.

All nonhydrogen atoms were refined anisotropically by full-matrix least-squares (SHELXL-2014). All hydrogen atoms were placed using a riding model. Their positions were constrained relative to their parent atom by using the appropriate HFIX command in SHELXL-2014. The absolute stereochemistry of the molecule was established by anomalous dispersion using the Parson's method with a Flack parameter of 0.002(230). Crystallographic data have been deposited at the Cambridge Crystallographic Data Center (CCDC number 1442028).

B. Experimental Cellular Procedures

1. Cell Culture:

Cell lines were purchased from American Type Culture Collection (ATCC) or Leibniz-Institute Deutsche Sammlung von Mikroorganismen and Zellkulturen GmbH (DSMZ) and cultured without antibiotics or as specified by the provider. All cell lines were incubated at 37° C. and were maintained in an atmosphere containing 5% CO$_2$ according to proper sterile cell culture practices [16]. The patient-derived triple-negative IBC cell line SUM-149 [17] and the ER/PR-negative/HER2-positive SUM-190 cell line (kind gifts from Dr. Steven Ethier, Medical University of South Carolina; both available at Asterand Bioscience, Detroit, MI) were cultured in Ham's F12 medium (Life Technologies, Carlsbad, CA) with 10% fetal bovine serum (FBS) as in [12, 14] and in Ham's F12 medium with 2% FBS, respectively. Adherent cells were grown to 80%-90% confluence, unless otherwise specified, and suspension cells were grown to densities recommended by Asterand, ATCC, or DSMZ before use. BJ (CRL-2522, normal human foreskin fibroblast), MCF-7 (HTB-22, human breast carcinoma) were cultured in EMEM medium (Life Technologies, Carlsbad, CA) with 10% FBS, and MDA-MB-231 (HTB-26, human breast carcinoma, triple-negative breast cancer) cells were cultured in DMEM medium (Life Technologies, Carlsbad, CA) supplemented with 10% FBS. Suspension cells KOPN8 (infant human B cell precursor acute lymphoblastic leukemia with MLL-MLLt1/ENL fusion), UoC-B1 (kindly gifted by Dr. William Evans of St. Jude Children's Research Hospital), SUP-B15 (ACC 389), NALM-06 (ACC 128) or BCR-ABL (murine B cell precursor acute lymphoblastic leukemia of pediatric relapsed ALL with BCR-ABL fusion) cells were cultured in RPMI media supplemented with 10% FBS. Cells were tested with MycoAlert™ *Mycoplasma* detection kit (Lonza) by using the manufacturer's conditions and were deemed negative. The cell lines were authenticated by IDEXX BioResearch (Columbia, MO).

2. CellTiter-Glo Viability Assay (CTG):

Either $1\times10^3$-$4.8\times10^3$ or $4\times10^2$-$1.2\times10^3$ cells were seeded to each well of 96- or 384-well white polystyrene flat-bottomed plates (3610 or 8804BC, Corning) in 100 μL or 30 μL media per well, respectively. The concentrations used were experimentally determined to ensure logarithmic growth during the duration of the experiment and prevent adverse effects on cell growth by DMSO exposure. The plates were incubated at 37° C. in 5% CO$_2$ for 24 h before treatment. Stock solutions of test compounds (10 mM in DMSO) in nine 3-fold serial dilutions were dispensed via pintool (Biomek). The final concentration of DMSO was 0.3% (v/v) in each well. The plates were incubated for 72 h at 37° C. in 5% CO$_2$ and then quenched with CellTiter-Glo® reagent (50 µL/well in 96-well plate, 30 µL/well in 384-well plate) at RT. The positive controls included staurosporine (10 µM), gambogic acid (10 µM), and a toxic quinoline generated in-house. Plates were then incubated at RT for 20 min and centrifuged at 1000 rpm for 1 min. The cytotoxicity assay was performed by using the CellTiterGlo Luminescent Cell Viability Assay kit (G7570, Promega, Madison, WI) according to the manufacturer's instructions. Luminescence was recorded in an Envision plate reader (Perkin Elmer).

3. ApoTox-Glo™ Triplex Assay:

Cells ($9.5 \times 10^4$/well in 75 µL of fresh medium) were dispensed in 96-well black flat bottom (8807BC, Corning) plates. The cells were incubated for 12 h at 37° C. and then treated with compounds (25 µL) for 24 h. DMSO was used as a negative control, and staurosporine was used as the positive control. The experiment was stopped by adding the Viability/Cytotoxicity Reagent and briefly mixed by orbital shaking (300-500 rpm for ~30 sec). Plates were incubated for 30 min at 37° C., and fluorescence was measured in an Envision plate reader at the following two wavelength sets: 400Ex/505Em (Viability) 485Ex/520Em (Cytotoxicity). Then, the Caspase-Glo® 3/7 Reagent was added; plates were mixed briefly by orbital shaking (300-500 rpm for ~30 sec), followed by an additional 30 min incubation at RT. Then luminescence, which correlates with caspase 3/7 activation, was recorded with a plate reader to determine apoptosis induction.

4. Cell Viability Assays:

Cell viability assays (MTT or PI staining assays) in SUM-149, SUM-190, MDA-MB-231, and MCF10A cells were performed as we previously described [14].

5. Colony Formation Assay:

SUM-149 cells ($1.5 \times 10^6$ cells/well) were plated on a 6-well plate. Two days later, cell media was changed to 5% FBS, and cells were incubated at 37° C. in a 5% $CO_2$ atmosphere for 1 h before vehicle (0.1% DMSO) or EP (5-40 µM) was added. After 72 h of treatment, cells were trypsinized and reseeded at 200 cells/mL per well in 24-well plates. After 10 d of culture, colonies were visualized by crystal violet staining, and the colony numbers were counted under a microscope.

6. De Novo In-Cell Protein Synthesis:

First, $2.5 \times 10^4$ cells/well were seeded in 8-well µ-slides (Ibidi®, #80826) and incubated at 37° C. for 12 h. The cells were treated with vehicle, compounds Ganoderic acid A or EP, or cycloheximide (positive control) for 2 h to determine protein synthesis as nascent proteins generated using Biovision's EZClick™ Global Protein Synthesis Assay Kit, (#K715-100, Milpitas, CA). The assay includes a robust chemical method based on an alkyne containing o-propargyl-puromycin (OP-puro) probe, which stops translation by forming covalent conjugates with nascent polypeptide chains. Truncated polypeptides are rapidly turned over by the proteasome and can be detected based on the subsequent click reaction with a fluorescent azide. The reaction was conducted according to the manufacturer's protocol. Cells were imaged at 20× with a Nikon C2 scanning confocal microscope, and the whole image montage was quantified by using Gen5 Software and Lionheart™ FX Automated Microscope (BioTek, Winooski, VT).

7. Reactive Oxygen Species (ROS) Measurement:

SUM-149 or MDA-MB-231 were plated in 96 well plates at a density of $2 \times 10^4$ and $1 \times 10^4$ cells/well, respectively in black 96-well clear bottom tissue culture plates and incubated for 24 h at 37° C. The mRuby-Mito-7 plasmid was obtained from Addgene (#55874 from Michael Davidson). A stable clone of MCF-7 was generated by using Fugene 6 (Roche) to transfect cells ($2 \times 10^5$) with plasmid (2.0 µg) under neomycin selection. A stable cell line was selected by using G418 (300 µg/mL) for 2 weeks, sorted by flow cytometry, and maintained under G418 thereafter. Transfected MCF-7 cells were plated at a density of $2 \times 10^4$ cells/well in black 96-well clear bottom tissue culture plates and incubated overnight at 37° C. To test for ROS formation and remove background, cells were replenished with fresh PBS with 2% FBS and treated with the desired compounds for 1 h at 37° C. DMSO (0.5%) was used as a negative control, while Menadione (Mena, at 10 µM) or t-Butyl hydroperoxide (TBHP) at 100 µM final concentration were used as a positive control. To evaluate the compounds' effects on ROS formation inhibition, the free radical scavenger N-acetyl cysteine (NAC) was used. Cells were treated with or without NAC (500 µM or 100 µM) for 1 h, then CellROX® green reagent (Molecular Probes #C10444) was added to a final concentration of 5 µM, and cells were incubated for an additional 30 min at 37° C. Cells were then washed 2× with PBS, followed by fixation with 4% paraformaldehyde (v/v) for 15 min, and 2 more washes with PBS. Fluorescence intensity was measured in a Clariostar® plate reader (BMG LABTECH, Cary, NC) at 535 nm.

8. Cell Cycle Assay:

SUM-149 cells were treated for 48 h with EP, then collected and washed in 1×PBS. The cells ($5 \times 10^5$) were fixed and permeabilized in 70% ethanol at −20° C. until further analysis. To measure the DNA content, the cells were washed and resuspended in 150 µL of PBS buffer then incubated in 100 µL of 100 µg/mL RNase A (MilliporeSigma, Burlington, MA) for 15 min at RT, then 250 µL of 50 µg/mL Propidium Iodide (MilliporeSigma) was added. Samples were incubated at RT for 10 min and analyzed on a BD FACS Canto II flow cytometer (BD Biosciences, San José, Calif.). Data were analyzed by using FlowJo software (V10, FlowJo LLC, Ashland, OR).

9. Annexin V Apoptosis Detection:

SUM-149 cells ($5 \times 10^5$) were seeded and treated either with vehicle (0.1% DMSO) or with 20 µM of EP or with puromycin (200 ng/mL) as positive control for 48 h. After treatment floating cells were collected, and all cells were harvested and counted. Treated cells were analyzed for cell death by using the FITC Annexin-V/7AAD Apoptosis detection kit (product #640922, Biolegend, San Diego, CA) according to the manufacturer's instructions. Briefly, cells were resuspended in Annexin Binding Buffer, stained with Annexin V-FITC and/or 7-AAD, and incubated for 30 min at 4° C. Data were acquired on a BD FACS Canto II cytometer (BD Biosciences, San José, Calif.) and analyzed by using FlowJo software (V10, FlowJo LLC, Ashland, OR).

10. Migration and Invasion Assays:

Cell migration and invasion were measured by using Corning® FluoroBlok™ Cell Culture Inserts and performing BD BioCoat Matrigel invasion assays (BD Biosciences, San José, Calif.) as described in [12, 14].

11. Immunoblots:

Breast cancer cells treated with vehicle or EP were lysed, and equal total protein was resolved via SDS-PAGE and immunoblotted with indicated antibodies (Cell Signaling Technologies, Abcam, Sigma) as described previously [12, 14, 18].

C. Statistical Analysis:

For the CTG assay, 3 or 4 replicate assays were conducted for each experimental condition, and a minimum of 3 independent experiments were conducted for cellular assays. The mean luminescence of each experimental treatment group was normalized as a percentage of the mean intensity of untreated controls. $EC_{50}$ values (µM) were calculated by Pipeline Pilot Software (Accelrys, Enterprise Platform, CA, USA). $EC_{50}$ values (µM) from the viability assay were calculated from dose response curve-fitting via non-linear regression by using GraphPad Prism (Version 7.0 San Diego, CA). For cell viability, colony formation, cell-cycle progression, cell death, and western blot assays, the analyses were performed via one-way or two-way ANOVA with post-testing for each condition (concentration, cell cycle stage, apoptotic event, cell line) by using GraphPad Prism.

TABLE 1

Cytotoxicity of EP probes via CTG assay. EC50 value expressed as the mean ± SD of three independent experiments.

| Number | MDA-MB231 EC50 (µM) | SUM149 EC50 (µM) | T47D EC50 (µM) | HMEC EC50 (µM) | TI(HMEC/SUM149) |
|---|---|---|---|---|---|
| Phosphoramide | >11 | >12 | ND | >10 | >1 |
| Doxorubicin | 1 | 1 | ND | >10 | >11 |
| Taxol | 2 | 0.01 | ND | >10 | >800 |
| Capecitabin | 5 | 5 | ND | 10 | >2 |
| 3 | 18 | 6 | 19 | >20 | >3 |
| 3a | 7 | 5 | 10 | >13 | >3 |
| 3b | 16 | 3 | >20 | >20 | >4 |
| 3c | >20 | 5 | >20 | >20 | >4 |
| 3d | >20 | 10 | >20 | >20 | >2 |
| 3e | 16 | 10 | >20 | >20 | >2 |
| 3f | 9 | 5 | >20 | >20 | >4 |
| 3g | 37 | 5 | >20 | >20 | >4 |
| 3h | 25 | 21 | 17 | >20 | >4 |
| 3i | 33 | 5 | 18 | >20 | >4 |
| 3j | 8 | 4 | 11 | >13 | >4 |
| 3k | 10 | 4 | >10 | >14 | >6 |
| 3l | 20 | 18 | >20 | >20 | >1 |
| 3m | 18 | 2 | 18 | >15 | >6 |

PUBLICATIONS CITED

These publications are incorporated by reference to the extent they relate materials and methods disclosed herein.
GLC Compounds
1 Chen, X., et al. (2006). International immunopharmacology. 6, 499-508.
2 Gao, Y., et al. (2003). Immunological investigations. 32, 201-215.
3 Jin, X., et al. (2016). Cochrane Database Syst Rev. 4, CD007731.
4 Suárez-Arroyo, I., et al. (2017). Medicines. 4, 15.
5 Paterson, R. R. (2006). Phytochemistry. 67, 1985-2001.
6 Liu, X., et al. (2002). Cancer Lett. 182, 155-161.
7 Min, B. et al. (2000). Chem Pharm Bull. 48, 1026-1033.
8 Xie, Y. et al. (2006). Enzyme Microb Technol 40, 177-185.
9 Huie, C. and Di, X. (2004). J Chromatogr B. 812, 241-257.
10 Wasser, S. P. and Weis, A. L. (1999). Int J Med Mushrooms. 1, 31-62.
11 Jong, S. C. and Donovick, R. (1989). Adv Appl Microbiol. 34, 183-261.
12 Martinez-Montemayor, M. M., et al. (2011). Nutrition and cancer. 63, 1085-1094.
13 Suarez-Arroyo, I. J., et al. (2013). PLoS One. 8, e57431.
14 Suarez-Arroyo, I. J., et al. (2016). J Cancer. 7, 500-511
15 Tu, Y., et al. (2010). J. Nat. Prod. 73, 751-754.
16 Hay, R. J., et al. (1992). ATCC Quality Control Methods for Cell Lines.
17 Ethier, S. P., et al. (1996). Cancer Res. 56, 899-907.
18 Castillo-Pichardo, L., (2009). Clin Exp Metastasis. 26, 505-516.
19 Borchers, A. T., et al. (1999). Proceedings of the Society for Experimental Biology and Medicine. 221, 281-293.
20 Boh, B., et al. (2007). Biotechnol Annu Rev. 13, 265-301.
21 Zhang, Y. Q. and Rao, R. (2010). Virulence. 1, 551-554.
22 Bernal, J. D. and Crowfoot, D. Y. (1935). Journal of the Chemical Society (Resumed), 93.
23 Bernal, J. D., et al. (1940). Cambridge University Press, London.
24 Cantrell, C., et al. (1999). Planta Medica. 65, 732-734.
25 Hull, S. E. and Woolfson, M. M. (1976). Acta Crystallographica Section B. 32, 2370-2373.
26 Guo, D., et al. (2004). Nature genetics. 36, 837-841.
27 Nam, K. et al. (2001). Life Sci. 69, 229-237.
28 Dai, J., et al. (2017). Oncotarget. 8, 13770-13781.
29 Liu, J., et al. (2012). Proc Natl Acad Sci USA. 109, 413-418.
30 Ling, T., et al. (2018). Eur J Med Chem. 146, 501-510.
31 Lehman, H. L., et al. (2012). Molecular Cancer Research. 10, 1306-1318.
32 Chin, Y., et al. (2014). Cancer discovery. 4, 942-955.
33 Adamec, J., (2009). J Sep Sci. 32, 4052-4058.
34 Thyagaraj an, A., et al. (2010). Nutr Cancer. 62, 630-640.
35 Thyagarajan-Sahu, A., et al. (2011). BMC Complement Altern Med. 11, 74.
36 Borchers, A., et al. (1999). Proceedings of the Society for Experimental Biology and Medicine. 221, 281-293.
37 Gao, Y., et al. (2005). Journal of medicinal food. 8, 159-168.
38 Joseph, S., et al. Acta pharmaceutica. 61, 335-342.
39 Lin, S. B., et al. (2003). Life Sci. 72, 2381-2390.
40 Lin, Z. B. (2005). J Pharmacol Sci. 99, 144-153.
41 Sliva, D. (2004). Mini Rev Med Chem. 4, 873-879.
42 Wang, Y. Y., et al. (2002). Bioorg Med Chem. 10, 1057-1062.
43 Zhang, G. L., et al. (2002). World J Gastroenterol. 8, 728-733.
44 Zhu, X. L., et al. (2007). J Ethnopharmacol. 111, 219-226.
45 Jiang, J., et al. (2008). Int J Mol Med. 21, 577-584.
46 Lee, S., (1998). Planta Med. 64, 303-308.
47 Smina, T. P., et al. (2011). Mutat Res. 726, 188-194.
48 Yao, D., et al. (2011). Molecular Cancer Research. 9, 1608-1620.
49 Zhang, D., et al. (2009). Clinical Cancer Research. 15, 6639-6648.
50 Robertson, F., et al. (2012). Clinical & Experimental Pathology. 2, 119.
51 Siddiqa, A., et al. (2008). BMC Cancer. 8, 129.
52 Brandes, L. J. et al. (1983). Cancer Res. 43, 2831-2835.
53 Cristofanilli, M., et al. (2007). Cancer. 110, 1436-1444.
54 Fernandez, S. V., et al. (2013). Breast Cancer Res Treat. 140, 23-33.
55 Silvera, D., et al. (2009). Nat Cell Biol. 11, 903-908.
56 Bu, M., et al. (2017). Chem Med Chem. 12, 466-474.
57 Posner, G. H., et al. (2004). J. Med. Chem. 47, 1299-1301.
58 Li, X., et al. (2015). Oncotarget. 6, 17832-17846.
59 Li, X., et al. (2016). Oncotarget. 7, 33948-33959.
60 Kang, J., et al. (2015). J Ethnopharmacology. 173, 303-312.
61 Hook, B. and Schagat, T. (2012). Profiling Compound Effects on Cell Health in a Time Course Using a Multiplexed Same-Well Assay.
62 Kobori, M., et al. (2007). Br J Pharmacol. 150, 209-219.

63 Kang, J. H., et al. (2015). J Ethnopharmacology. 173, 303-312.
64 Russo, A., et al. (2010). Chemic-Biological Interactions. 184, 352-358.
65 Takei, T., et al. (2005). Biotechnol. Biochem. 69, 212-215.
66 He, L., et al. (2018). International journal of molecular sciences. 19, 3935.

EP Probes
1 T. Nakanishi, et al. *J Nat Med.* 1998, 52, 521-526.
2 K. Yasukawa, et al. *Biol Pharm Bull.* 1996, 19, 573-576.
3 Y. Takahashi, et al. *Phytochemistry.* 1991, 30, 4117-4120.
4 C. Jiménez, et al. *J Nat Prod.* 1989, 52, 619-622.
5 M. C. Deghrigue, et al. *J Pharmaceut Sci.* 2014, 22, 64.
6 (a) W. Qing-Ping, et al. *PLoS One.* 2012, 7: 44579. (b) D. B. Graca Sgarbi et al. Mycopathologia. 1997, 139, 9-14.
7 (a) J. M. Gao, et al. *Phytomedicine.* 2007, 14, 821-824. (b) Angel Ramos-Ligonio et al. Phytother. Res. 2012, 26, 938-943. (c) L. Ma, et al., Food Chem, 2013, 139, 503-508.
8 M. Kobori, et al. *Br J Pharmacol.* 2007, 150, 209-219.
9 N. Duarte, et al. *Phytother. Res.* 2007, 21, 601-604.
10 (a) M. Bu, et al. *Chem Med Chem.* 2017, 12, 466-474. (b) M. Bu, et al. *Bioorg Med Chem Lett.* 2017, 27, 3856-3861. (c) G. Battogtokh, et al. *Acta Pharmaceutica Sinica B.* 2018, 8, 862-880.
11 M. M. Martinez-Montemayor, et al. *Accepted to Frontiers in Pharmacology,* Jan. 10, 2019.
12 I. Fernandez, A. Robert. *Org. Biomol. Chem.* 2011, 9, 4098-4107.
13 M. Axelrod, et al. *Oncotarget.* 2013, 4, 622-635.
14 S. M. Mense, L. Zhang. *Cell Res.,* 2006, 16, 681-692.
15 D. Chiabrando, et al. *Front. Pharmacol.,* 2014, 5, 1-24.
16 (a) R. Chiorean, et al. 2013, 22, 1026-1033. (b) K. J. Chavez, V. Sireesha, S. V. Garimella, S. Lipkowitz. *Breast Dis.* 2010, 32, 35-48. (c) W. D. Foulkes, et al. *N Engl J Med.* 2010, 363, 1938-1948.
17 H. Y. Wu, et al. *Sci Rep.* 2018, 8, 17956.
18 Z. Zhang, et al. *Redox Biol.* 2018, S2213-2317(18) 30895-4.
19 C. Florean, et al. *Free Radic Biol Med.* 2019, S0891-5849(18)32332-3.
20 (a) H. M. Schipper, et al. *Exp Cell Res.* 1993, 207, 62-7. (b) Y. Han, et al. *Nat Commun.* 2017, 8, 1307.
21 C. S. McKay, M. G. Finn. *Chem Biol.,* 2014, 21, 1075-101.
22 T. Ling, et al. *Eur J Med Chem.* 2018, 146, 501-510.
23 (a) R. S. Ames, et al., *Expert Opin Drug Discov.* 2007, 12, 1669-81(BACMan techn). (b) Addgene plasmid #54840 deposited by Dr. M. Davidson.
24 T. Böttcher, et al. *Angew Chem Int Ed Engl.* 2010, 49, 2680-98.
25 T. Wang, et al. *Mol Biol Cell.* 2004, 15, 815-26.
26 K. W. Huh, et al. *Proc Natl Acad Sci USA.* 2005, 102, 11492-7.

The invention claimed is:

1. A method of modifying a cancer-related symptom in a subject, said method comprising the step of administering a pharmaceutical composition comprising a *Ganoderma lucidum* derivative to the subject, wherein the pharmaceutical composition modifies the cancer-related symptom, and wherein the *Ganoderma lucidum* derivative is selected from the group consisting of ergosterol sulfonamide, 5-6-dihydroergosterol sulfonamide, ergosterol peroxide sulfonamide, and any combination thereof.

2. The method of claim 1, wherein the modification of the cancer-related symptom is selected from the group consisting of a reduction in a tumor volume, an inhibition of cancer cell viability, an induction of anti-proliferative activity of cancer cells, an induction of cell cycle arrest of cancer cells, an induction of apoptosis of cancer cells, an induction of PARP cleavage of cancer cells, an induction of apoptosis of cancer cells, a decrease in cancer cell migration, a decrease in cancer cell invasiveness, an induction of reactive oxygen species (ROS) and combinations thereof.

3. The method of claim 1, wherein the subject has breast cancer.

4. The method of claim 3, wherein the breast cancer is an inflammatory breast cancer.

5. A method of treating cancer in a subject, said method comprising the step of administering a pharmaceutical composition comprising a *Ganoderma lucidum* derivative to the subject, and wherein the *Ganoderma lucidum* derivative is selected from the group consisting of ergosterol sulfonamide, 5-6-dihydroergosterol sulfonamide, ergosterol peroxide sulfonamide, and any combination thereof.

6. The method of claim 5, wherein the cancer is breast cancer.

7. The method of claim 6, wherein the breast cancer is inflammatory breast cancer.

8. The method of claim 1, wherein the *Ganoderma lucidum* derivative comprises ergosterol sulfonamide.

9. The method of claim 1, wherein the *Ganoderma lucidum* derivative comprises 5-6-dihydroergosterol sulfonamide.

10. The method of claim 1, wherein the *Ganoderma lucidum* derivative comprises ergosterol peroxide sulfonamide.

11. The method of claim 5, wherein the *Ganoderma lucidum* derivative comprises ergosterol sulfonamide.

12. The method of claim 5, wherein the *Ganoderma lucidum* derivative comprises 5-6-dihydroergosterol sulfonamide.

13. The method of claim 5, wherein the *Ganoderma lucidum* derivative comprises ergosterol peroxide sulfonamide.

* * * * *